United States Patent
Dhawan et al.

(10) Patent No.: US 11,932,795 B2
(45) Date of Patent: Mar. 19, 2024

(54) AROMATIC AMINE EPOXIDE ADDUCTS FOR CORROSION INHIBITION

(71) Applicant: Ecolab USA Inc., St. Paul, MN (US)

(72) Inventors: Ashish Dhawan, Aurora, IL (US); Jeremy Moloney, Katy, TX (US); Carter Martin Silvernail, Lakeville, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 17/337,690

(22) Filed: Jun. 3, 2021

(65) Prior Publication Data

US 2021/0380883 A1    Dec. 9, 2021

Related U.S. Application Data

(60) Provisional application No. 63/033,972, filed on Jun. 3, 2020.

(51) Int. Cl.
| | |
|---|---|
| C23F 11/14 | (2006.01) |
| C07C 217/76 | (2006.01) |
| C09K 15/20 | (2006.01) |
| C09K 15/24 | (2006.01) |

(52) U.S. Cl.
CPC ............ C09K 15/24 (2013.01); C07C 217/76 (2013.01); C09K 15/20 (2013.01); C23F 11/14 (2013.01); C23F 11/142 (2013.01)

(58) Field of Classification Search
CPC ........... C23F 11/04; C23F 11/10; C23F 11/12; C23F 11/122; C23F 11/14; C23F 11/141; C23F 11/142; C09K 15/18; C09K 15/20; C09K 15/24; C07C 215/74; C07C 215/76; C07C 215/78; C07C 215/84; C07C 215/86; C07C 215/88; C07C 217/76; C07C 217/78; C07C 217/80; C07C 217/82; C07C 217/86; C07C 217/88; C07C 217/90; C07C 217/92; C07C 217/94; C07C 2601/16
See application file for complete search history.

(56) References Cited

U.S. PATENT DOCUMENTS

| | | | | |
|---|---|---|---|---|
| 2,415,009 A | * | 1/1947 | Hatch ....................... | C07C 7/20 526/217 |
| 2,797,152 A | * | 6/1957 | Hughes .................. | C10L 1/2235 252/392 |
| 3,000,852 A | * | 9/1961 | Merz ........................ | C08K 5/18 252/401 |
| 3,472,666 A | * | 10/1969 | Foroulis .................. | C23F 11/04 252/390 |
| 3,728,281 A | * | 4/1973 | Marks ..................... | C23F 11/08 252/393 |
| 4,148,772 A | | 4/1979 | Marchetti et al. | |
| 4,374,965 A | | 2/1983 | Dickie et al. | |

(Continued)

FOREIGN PATENT DOCUMENTS

| | | |
|---|---|---|
| DE | 2348576 A1 | 4/1975 |
| EP | 1777288 B1 | 7/2009 |

(Continued)

OTHER PUBLICATIONS

Liu et al. ("Aryl aminoalcohols as corrosion inhibitors for carbon steel in chloride-contaminated simulated concrete pour solution," Int. J. Electrochem. Sci., 11, 2016, 1135-1151) (Year: 2016).*
Arukula et al. ("Investigations on anticorrosive, thermal, and mechanical properties of conducting polyurethanes with tetraaniline pendent groups," Polym. Adv. Technol., 2018, 29, 1620-1631) (Year: 2018).*
Sherif et al. ("Inhibition of copper corrosion in 3.0% NaCl solution by N-phenyl-1,4,-phenylenediamine," Journal of The Electrochemical Society, 152, 10, B428-B433, 2005) (Year: 2005).*
Ekblad, Tobias et al., Poly(ethylene glycol)-Containing Hydrogel Surfaces for Antifouling Applications in Marine and Freshwater Environments, Biomacromolecules 2008, 9, pp. 2775-2783.
Falk, Nancy A., Surfactants as Antimicrobials: A Brief Overview of Microbial Interfacial Chemistry and Surfactant Antimicrobial Activity, J. Surfact Deterg (2019) 22, pp. 1119-1127.

(Continued)

*Primary Examiner* — Matthew R Diaz
(74) *Attorney, Agent, or Firm* — Stinson LLP

(57) ABSTRACT

Compositions and methods are provided for reducing, inhibiting, or preventing corrosion of a surface, the method comprising contacting an anticorrosion compound of Formula 1 with the surface, the anticorrosion compound of Formula 1 having a structure corresponding to:

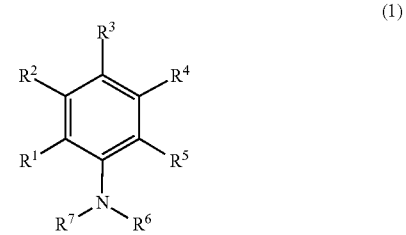

(1)

wherein $R^1$, $R^2$, $R^3$, $R^4$, and $R^5$ are independently selected from hydrogen, hydroxyl, alkyl, alkoxyl, aryl, alkaryl, aralkyl, and $-NR^8R^9$; $R^6$ and $R^7$ are independently hydrogen, a substituted alkyl, substituted alkenyl, substituted aryl, substituted alkaryl, or substituted aralkyl, wherein at least one substituent is a hydroxyl or an ether; provided that at least one of $R^6$ and $R^7$ is other than hydrogen; $R^8$ and $R^9$ are independently hydrogen, unsubstituted alkyl, unsubstituted alkenyl, unsubstituted aryl, unsubstituted alkaryl, unsubstituted aralkyl, substituted alkyl, substituted alkenyl, or substituted alkaryl, wherein at least one substituent is a hydroxyl or an ether; or any two adjacent groups of $R^1$, $R^2$, $R^3$, $R^4$, and $R^5$ form one or more ring structures.

19 Claims, 1 Drawing Sheet

(56) References Cited

U.S. PATENT DOCUMENTS

| | | | |
|---|---|---|---|
| 4,386,939 A * | 6/1983 | Lange | C10M 133/14 |
| | | | 564/399 |
| 4,655,287 A | 4/1987 | Wu | |
| 4,664,811 A | 5/1987 | Operhofer | |
| 4,728,497 A * | 3/1988 | Muccitelli | C23F 11/142 |
| | | | 252/392 |
| 4,770,790 A | 9/1988 | Oberhofer | |
| 4,808,441 A | 2/1989 | Chattha et al. | |
| 4,851,421 A | 7/1989 | Iwasaki et al. | |
| 5,057,556 A | 10/1991 | Redman | |
| 5,318,805 A | 6/1994 | Wu | |
| 5,344,674 A | 9/1994 | Wu | |
| 5,380,781 A | 1/1995 | Kato et al. | |
| 5,447,974 A | 9/1995 | Peng | |
| 5,503,836 A | 4/1996 | Fellers et al. | |
| 5,756,221 A | 5/1998 | Horibe et al. | |
| 5,770,549 A | 6/1998 | Gross | |
| 5,853,462 A * | 12/1998 | Spellane | C23F 11/164 |
| | | | 252/390 |
| 5,876,514 A | 3/1999 | Rolando et al. | |
| 5,906,864 A | 5/1999 | Osterhold et al. | |
| 6,096,225 A | 8/2000 | Yang et al. | |
| 6,120,705 A * | 9/2000 | Spellane | C09D 5/086 |
| | | | 106/14.37 |
| 6,139,830 A | 10/2000 | Donlan et al. | |
| 6,207,731 B1 | 3/2001 | Gam | |
| 6,653,370 B2 | 11/2003 | Paar et al. | |
| 6,670,041 B2 | 12/2003 | Paar et al. | |
| 6,835,459 B2 | 12/2004 | Lorenz et al. | |
| 6,911,490 B2 | 6/2005 | Feola et al. | |
| 7,141,538 B2 | 11/2006 | Noguchi et al. | |
| 7,165,561 B2 | 1/2007 | Baldridge et al. | |
| 7,414,162 B2 * | 8/2008 | Link | C09K 15/28 |
| | | | 585/5 |
| 7,470,755 B2 | 12/2008 | Abrami et al. | |
| 8,445,585 B2 | 5/2013 | Paar et al. | |
| 8,501,997 B2 | 8/2013 | Vedage et al. | |
| 8,512,594 B2 | 8/2013 | Walker et al. | |
| 8,809,392 B2 | 8/2014 | Li et al. | |
| 8,901,063 B2 | 12/2014 | Soontravanich et al. | |
| 8,927,479 B2 | 1/2015 | Perlas | |
| 9,522,974 B2 | 12/2016 | Barriau et al. | |
| 9,663,431 B2 | 5/2017 | Griese et al. | |
| 9,670,433 B1 | 6/2017 | Hodge et al. | |
| 9,719,057 B2 | 8/2017 | Nielsen et al. | |
| 9,809,719 B2 | 11/2017 | Paar et al. | |
| 9,850,388 B2 | 12/2017 | Paar et al. | |
| 9,889,466 B2 | 2/2018 | Grabbe et al. | |
| 10,266,794 B2 | 4/2019 | Hunt, Jr. et al. | |
| 10,273,433 B2 | 4/2019 | Man et al. | |
| 10,308,886 B2 * | 6/2019 | Rana | C10G 29/20 |
| 10,351,801 B2 | 7/2019 | Martinez-Crowley et al. | |
| 10,479,959 B2 | 11/2019 | Creamer et al. | |
| 2003/0096725 A1 | 5/2003 | Tsibouklis et al. | |
| 2003/0173302 A1 | 9/2003 | Xiong et al. | |
| 2008/0108539 A1 | 5/2008 | Kany et al. | |
| 2009/0166291 A1 | 7/2009 | Jackson | |
| 2009/0270566 A1 | 10/2009 | Thorman et al. | |
| 2011/0071069 A1 | 3/2011 | Konishi et al. | |
| 2012/0232169 A1 | 9/2012 | Wu et al. | |
| 2013/0126113 A1 | 5/2013 | Tan et al. | |
| 2015/0080282 A1 | 3/2015 | Krishna et al. | |
| 2018/0163020 A1 | 6/2018 | Zong et al. | |
| 2018/0223112 A1 | 8/2018 | Jaquess | |
| 2018/0355284 A1 | 12/2018 | Bhole et al. | |
| 2019/0144314 A1 * | 5/2019 | Lin | C23F 11/14 |
| | | | 252/178 |
| 2019/0177661 A1 | 6/2019 | Walters et al. | |
| 2019/0264139 A1 | 8/2019 | Lant et al. | |
| 2020/0172831 A1 | 6/2020 | Dhawan et al. | |

FOREIGN PATENT DOCUMENTS

| | | | |
|---|---|---|---|
| EP | 3415571 A1 | 12/2018 | |
| WO | 2006/025928 A3 | 3/2006 | |
| WO | 2007/008199 A1 | 1/2007 | |
| WO | 2008/036559 A2 | 3/2008 | |
| WO | 2019/067173 A1 | 4/2019 | |
| WO | 2020/113218 A2 | 6/2020 | |

OTHER PUBLICATIONS

Database CA [Online], Chemical Abstracts Service, Columbus, Ohio, US. Sun, Yu et al., Process for preparation of temperature resistant salt resistant polyether sulfonate, Database Accession No. 2013:638115; & CN 103 058 895 A (Jiangsu Maysta Chemical Co., Ltd.) Apr. 24, 2013, 3 pages.

Database CA [Online], Chemical Abstracts Service, Columbus, Ohio, US. Wang, Dongfang et al., Study on the Interfacial tension of the water solution of a new anionic-non-ionic surfactant and crude oil, Database Accession No. 2009:578202; Xi'an Shiyou Daxue Xuebao, Ziran Kexueban (2008) 23(6), 70-73, 2 pages.

Mohamed Heba A. et al., Aromatic Amine-Epoxidized Sunflower Free-Fatty-Acid Adducts as Corrosion Inhibitors in Epoxy-Curable Varnishes, Journal of Applied Polymer Science, vol. 124, (2012), pp. 2007-2015.

* cited by examiner

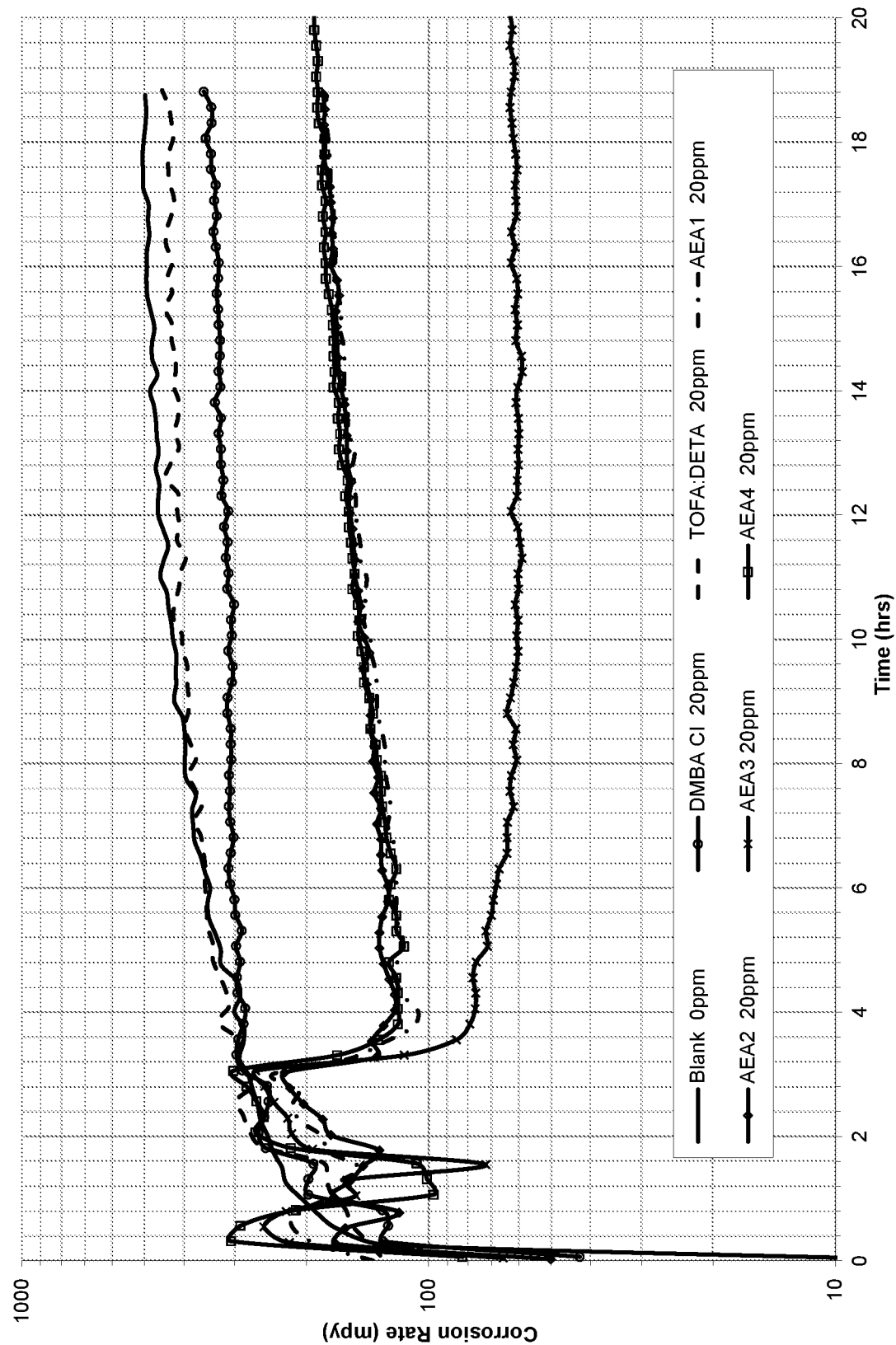

AROMATIC AMINE EPOXIDE ADDUCTS FOR CORROSION INHIBITION

CROSS REFERENCE TO RELATED APPLICATIONS

This application claims priority to U.S. Provisional Patent Application Ser. No. 63/033,972 filed on Jun. 3, 2020, the disclosure of which is incorporated herein by reference in its entirety.

FIELD OF THE INVENTION

Methods of using corrosion inhibitor compounds and compositions are provided for inhibiting corrosion at a surface of an industrial piece of equipment and for providing protection to the equipment against corrosive fluids and gases.

BACKGROUND OF THE INVENTION

Corrosion of metal surfaces in aqueous media has long been a problem for industries such as the oil and gas industry, food/beverage industry, wash/sanitizing industry, pulp and paper, power generation, manufacturing, and utilizes. For example, it is well known that during the production of oil and gas several other corrosive components are present such as brines, organic acids, carbon dioxide, hydrogen sulfide, and microorganisms. These aggressive constituents can cause severe corrosion as evidenced by surface pitting, embrittlement, and general loss of metal. The metallic surfaces can be composed of high alloy steels including chrome steels, ferritic alloy steels, austenitic stainless steels, precipitation-hardened stainless steels, and high nickel content steels, copper, and carbon steels.

In the food/beverage and wash/sanitizing industry, solutions such as sodium hypochlorite solutions are commonly used and are highly effective as bleaches and sanitizers for cleaning a variety of surfaces. However, sodium hypochlorite solutions are corrosive to many treated surfaces, in particular, metal surfaces become highly corroded.

There are several mechanisms responsible for corrosion of metals. In corrosive water systems, the overall corrosion rate is controlled by the reduction of oxygen inhibiting the cathodic reaction. However, the most robust and cost effective water treatment programs include both anodic and cathodic inhibitors to block reactions at both the anode and the cathode.

Mitigation of corrosion and fouling is essential in all water based or aqueous systems. As such, there exists a need for corrosion inhibitor compositions that are effective and environmentally friendly.

BRIEF SUMMARY OF THE INVENTION

Disclosed herein are methods for reducing, inhibiting, or preventing corrosion of a surface, the method comprising contacting an anticorrosion compound of Formula 1 with the surface, the anticorrosion compound of Formula 1 having a structure corresponding to:

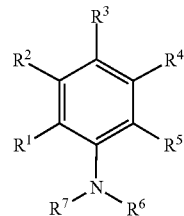

(1)

wherein $R^1$, $R^2$, $R^3$, $R^4$, and $R^5$ are independently selected from hydrogen, hydroxyl, alkyl, alkoxyl, aryl, alkaryl, aralkyl, and —$NR^8R^9$; $R^6$ and $R^7$ are independently hydrogen, a substituted alkyl, substituted alkenyl, substituted aryl, substituted alkaryl, or substituted aralkyl, wherein at least one substituent is a hydroxyl or an ether; provided that at least one of $R^6$ and $R^7$ is other than hydrogen; $R^8$ and $R^9$ are independently hydrogen, unsubstituted alkyl, unsubstituted alkenyl, unsubstituted aryl, unsubstituted alkaryl, unsubstituted aralkyl, substituted alkyl, substituted alkenyl, or substituted alkaryl, wherein at least one substituent is a hydroxyl or an ether; or any two adjacent groups of $R^1$, $R^2$, $R^3$, $R^4$, and $R^5$ form one or more ring structures.

The anticorrosion compound of Formula 1 can be added to a fluid in contact with the surface.

In the methods described herein, the surface can comprise a metal.

The substituted alkyl, substituted alkenyl, substituted aryl, substituted alkaryl, or substituted aralkyl of the compound of Formula 1 are substituted with a hydroxyl and an ether group.

For the compounds of Formula 1, at least one of $R^1$, $R^2$, $R^3$, $R^4$, and $R^5$ is hydroxyl or —$NR^8R^9$.

For the compounds of Formula 1, $R^3$ can be hydroxyl; or $R^3$ can be —$NR^8R^9$, wherein $R^8$ is hydrogen and $R^9$ is phenyl or substituted alkyl.

In the methods described herein, the anticorrosion compound of Formula 1 can correspond to the structure of Formula 2:

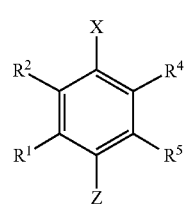

(2)

wherein Z has the structure corresponding to Z1 or Z2:

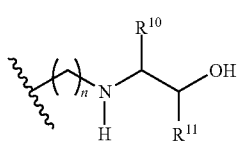

(Z1)

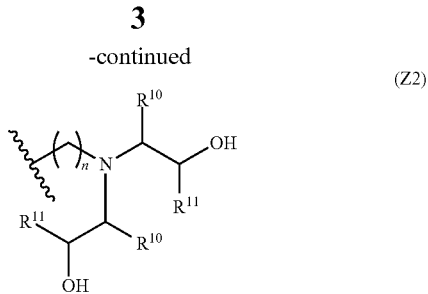

(Z2)

wherein X is hydroxyl, —NR$^8$R$^9$, or Z; n is an integer from 0 to 10; R$^{10}$ is independently hydrogen, alkyl, or aryl; R$^{11}$ is alkyl, aryl, or —(CH$_2$)z-O—R$^{12}$; R$^{12}$ is hydrogen or alkyl; and z is an integer from 1 to 10.

The methods can have the compounds of Formula 2, wherein X is hydroxyl.

The compounds of Formula 2 can have X is —NR$^8$R$^9$, wherein R$^8$ is hydrogen and R$^9$ is aryl; preferably, X is —NR$^8$R$^9$, wherein R$^8$ is hydrogen and R$^9$ is phenyl.

Additionally, the compound of Formula 2 can have X be Z and Z correspond to Z1.

The methods described herein wherein the compound of Formula 2 has n of 0, R$^{10}$ of hydrogen; and R$^{11}$ of (CH$_2$) z-O—R$^{12}$; preferably, z is 1 and R$^{12}$ is alkyl; more preferably, R$^{12}$ is C$_4$ to C$_{10}$ alkyl; most preferably, R$^{12}$ is butyl, pentyl, hexyl, heptyl, or octyl.

The compounds of Formula 2 can have Z be Z1. For these compounds, preferably, n is 0, R$^{10}$ is hydrogen; and R$^{11}$ is —(CH$_2$)z-O—R$^{12}$; preferably, z is 1 and R$^{12}$ is alkyl; more preferably, R$^{12}$ is C$_4$ to C$_{10}$ alkyl; most preferably, R$^{12}$ is butyl, pentyl, hexyl, heptyl, or octyl.

The compounds of Formula 2 can also have Z be Z2. For these compounds, n is 0, R$^{10}$ is hydrogen; and R$^{11}$ is —(CH$_2$)z-O—R$^{12}$; preferably, z is 1 and R$^{12}$ is alkyl; more preferably, R$^{12}$ is C$_4$ to C$_{10}$ alkyl; most preferably, R$^{12}$ is butyl, pentyl, hexyl, heptyl, or octyl.

For the methods described herein, the compounds of Formula 1 or 2 can have R$^1$, R$^2$, R$^4$, and R$^5$ be hydrogen.

In the methods described herein, the anticorrosion compound is selected from the group consisting of: 4-[(2-hydroxyethyl)amino]phenol, 4-[(2-hydroxypropyl)amino] phenol, 4-[(2-hydroxybutyl)amino]phenol, 4-[(2-hydroxypentyl)amino]phenol, 4-[(2-hydroxyhexyl)amino] phenol, 4-[(2-hydroxy-2-phenylethyl)amino]phenol, 4-[(2-hydroxyheptyl)amino]phenol, 4-[(2-hydroxyoctyl)amino]phenol, 4-[(2-hydroxynonyl)amino]phenol, 4-[(2-hydroxydecyl)amino]phenol, 4-[(2-hydroxyundecyl)amino]phenol, 4-[(2-hydroxydodecyl)amino]phenol, 4-[(2-hydroxytridecyl)amino]phenol, 4-[(2-hydroxytetradecyl)amino]phenol, 4-[(2-hydroxypentadecyl)amino]phenol, 4-[(2-hydroxyhexadecyl)amino]phenol, 4-[(2-hydroxyheptadecyl)amino]phenol, 4-[(2-hydroxyoctadecyl)amino]phenol, 4-[(2-hydroxyeleyl)amino]phenol, 4-[(2-hydroxynonadecyl)amino]phenol, 4-[(2-hydroxyeicosyl)amino]phenol, 4-[(2-hydroxyheneicosyl)amino]phenol, 4-[(2-hydroxydocosyl)amino]phenol, and 4-[(2-hydroxytricosyl)amino]phenol.

The anticorrosion compound also can be selected from the group consisting of: 4-[bis(2-hydroxyethyl)amino]phenol, 4-[bis(2-hydroxypropyl)amino]phenol, 4-[bis(2-hydroxybutyl)amino]phenol, 4-[bis(2-hydroxypentyl)amino]phenol, 4-[bis(2-hydroxyhexyl)amino]phenol, 4-[bis(2-hydroxy-2-phenylethyl)amino]phenol, 4-[bis(2-hydroxyheptyl)amino]phenol, 4-[bis(2-hydroxyoctyl)amino]phenol, 4-[bis(2-hydroxynonyl)amino]phenol, 4-[bis(2-hydroxydecyl)amino] phenol, 4-[bis(2-hydroxyundecyl)amino]phenol, 4-[bis(2-hydroxydodecyl)amino]phenol, 4-[bis(2-hydroxytridecyl)amino]phenol, 4-[bis(2-hydroxytetradecyl)amino]phenol, 4-[bis(2-hydroxypentadecyl)amino]phenol, 4-[bis(2-hydroxyhexadecyl)amino]phenol, 4-[bis(2-hydroxyheptadecyl)amino]phenol, 4-[bis(2-hydroxyoctadecyl)amino]phenol, 4-[bis(2-hydroxyeleyl)amino]phenol, 4-[bis(2-hydroxynonadecyl)amino]phenol, 4-[bis(2-hydroxyeicosyl)amino]phenol, 4-[bis(2-hydroxyheneicosyl)amino]phenol, and 4-[bis(2-hydroxydocosyl)amino]phenol.

The anticorrosion compound can further be selected from the group consisting of: 4-[(methoxymethyl)amino]phenol, 4-[(2-methoxyethyl)amino]phenol, 4-[(3-methoxypropyl) amino]phenol, 4-[(4-methoxybutyl)amino]phenol, 4-[(5-methoxypentyl)amino]phenol, 4-[(6-methoxyhexyl)amino] phenol, 4-[(methoxyphenyl)amino]phenol, 4-[(ethoxymethyl)amino]phenol, 4-[(2-ethoxyethyl)amino] phenol, 4-[(3-ethoxypropyl)amino]phenol, 4-[(4-ethoxybutyl)amino]phenol, 4-[(5-ethoxypentyl)amino]phenol, 4-[(6-ethoxyhexyl)amino]phenol, 4-[(ethoxyphenyl)amino] phenol, 4-[(propoxymethyl)amino]phenol, 4-[(2-propoxyethyl)amino]phenol, 4-[(3-propoxypropyl)amino]phenol, 4-[(4-propoxybutyl)amino]phenol, 4-[(5-propoxypentyl) amino]phenol, 4-[(6-propoxyhexyl)amino]phenol, 4-[(propoxyphenyl)amino]phenol, 4-[(butoxymethyl) amino]phenol, 4-[(2-butoxyethyl)amino]phenol, 4-[(3-butoxypropyl)amino]phenol, 4-[(4-butoxybutyl)amino]phenol, 4-[(5-butoxypentyl)amino]phenol, 4-[(6-butoxyhexyl) amino]phenol, and 4-[(butoxyphenyl)amino]phenol.

The anticorrosion compound can be selected from the group consisting of: 4-[bis(methoxymethyl)amino]phenol, 4-[bis(2-methoxyethyl)amino]phenol, 4-[bis(3-methoxypropyl)amino]phenol, 4-[bis(4-methoxybutyl)amino]phenol, 4-[bis(5-methoxypentyl)amino]phenol, 4-[bis(6-methoxyhexyl)amino]phenol, 4-[bis(methoxyphenyl)amino]phenol, 4-[bis(ethoxymethyl)amino]phenol, 4-[bis(2-ethoxyethyl) amino]phenol, 4-[bis(3-ethoxypropyl)amino]phenol, 4-[bis (4-ethoxybutyl)amino]phenol, 4-[bis(5-ethoxypentyl) amino]phenol, 4-[bis(6-ethoxyhexyl)amino]phenol, 4-[bis (ethoxyphenyl)amino]phenol, 4-[bis(propoxymethyl) amino]phenol, 4-[bis(2-propoxyethyl)amino]phenol, 4-[bis (3-propoxypropyl)amino]phenol, 4-[bis(4-propoxybutyl) amino]phenol, 4-[bis(5-propoxypentyl)amino]phenol, 4-[bis(6-propoxyhexyl)amino]phenol, 4-[bis(propoxyphenyl)amino]phenol, 4-[bis(butoxymethyl)amino]phenol, 4-[bis(2-butoxyethyl)amino]phenol, 4-[bis(3-butoxypropyl) amino]phenol, 4-[bis(4-butoxybutyl)amino]phenol, 4-[bis (5-butoxypentyl)amino]phenol, 4-[bis(6-butoxyhexyl) amino]phenol, and 4-[bis(butoxyphenyl)amino]phenol.

The anticorrosion compound can also be selected from the group consisting of: 4-[(3-methoxy-2-hydroxy-propyl) amino]phenol, 4-[(3-ethoxy-2-hydroxy-propyl)amino]phenol, 4-[(3-propoxy-2-hydroxy-propyl)amino]phenol, 4-[(3-butoxy-2-hydroxy-propyl)amino]phenol, 4-[(3-pentyloxy-2-hydroxy-propyl)amino]phenol, 4-[(3-hexyloxy-2-hydroxy-propyl)amino]phenol, 4-[(3-heptyloxy-2-hydroxy-propyl)amino]phenol, 4-[(3-octyloxy-2-hydroxy-propyl) amino]phenol, 4-[(3-nonyloxy-2-hydroxy-propyl)amino] phenol, 4-[(3-decyloxy-2-hydroxy-propyl)amino]phenol, 4-[(3-undecyloxy-2-hydroxy-propyl)amino]phenol, 4-[(3-dodecyloxy-2-hydroxy-propyl)amino]phenol, 4-[(3-tridecyloxy-2-hydroxy-propyl)amino]phenol, 4-[(3-tetradecyloxy-2-hydroxy-propyl)amino]phenol, 4-[(3-pentadecyloxy-2-hydroxy-propyl)amino]phenol, 4-[(3-hexadecyloxy-2-hydroxy-propyl)amino]phenol, 4-[(3-heptadecyloxy-2-hydroxy-propyl)amino]phenol, 4-[(3-octadecyloxy-2-hydroxy-propyl)amino]phenol, 4-[(3-eleyloxy-2-hydroxypropyl)amino]phenol, 4-[(3-nonadecyloxy-2-hydroxy-propyl)amino]phenol, 4-[(3-eicosyloxy-2-hydroxy-propyl)amino]phenol, 4-[(3-heneicosyloxy-2-hydroxy-propyl)amino]phenol, 4-[(3-docosyloxy-2-hydroxy-propyl)amino]phenol, 4-[(3-tricosyloxy-2-hydroxy-propyl)amino]phenol, and 4-[bis(3-(2-ethylhexyl)oxy-2-hydroxy-propyl)amino]phenol.

The anticorrosion compound is additionally selected from the group consisting of: 4-[bis(3-methoxy-2-hydroxy-propyl)amino]phenol, 4-[bis(3-ethoxy-2-hydroxy-propyl)amino]phenol, 4-[bis(3-propoxy-2-hydroxy-propyl)amino]phenol, 4-[bis(3-butoxy-2-hydroxy-propyl)amino]phenol, 4-[bis(3-pentyloxy-2-hydroxy-propyl)amino]phenol, 4-[bis(3-hexyloxy-2-hydroxy-propyl)amino]phenol, 4-[bis(3-heptyloxy-2-hydroxy-propyl)amino]phenol, 4-[bis(3-octyloxy-2-hydroxy-propyl)amino]phenol, 4-[bis(3-nonyloxy-2-hydroxy-propyl)amino]phenol, 4-[bis(3-decyloxy-2-hydroxy-propyl)amino]phenol, 4-[bis(3-undecyloxy-2-hydroxy-propyl)amino]phenol, 4-[bis(3-dodecyloxy-2-hydroxy-propyl)amino]phenol, 4-[bis(3-tridecyloxy-2-hydroxy-propyl)amino]phenol, 4-[bis(3-tetradecyloxy-2-hydroxy-propyl)amino]phenol, 4-[bis(3-pentadecyloxy-2-hydroxy-propyl)amino]phenol, 4-[bis(3-hexadecyloxy-2-hydroxy-propyl)amino]phenol, 4-[bis(3-heptadecyloxy-2-hydroxy-propyl)amino]phenol, 4-[bis(3-octadecyloxy-2-hydroxy-propyl)amino]phenol, 4-[bis(3-eleyloxy-2-hydroxy-propyl)amino]phenol, 4-[bis(3-nonadecyloxy-2-hydroxy-propyl)amino]phenol, 4-[bis(3-eicosyloxy-2-hydroxy-propyl)amino]phenol, 4-[bis(3-heneicosyloxy-2-hydroxy-propyl)amino]phenol, 4-[bis(3-docosyloxy-2-hydroxy-propyl)amino]phenol, 4-[bis(3-tricosyloxy-2-hydroxy-propyl)amino]phenol, and 4-[bis(3-(2-ethylhexyl)oxy-2-hydroxy-propyl)amino]phenol.

The anticorrosion compound is also selected from the group consisting of: 1,4-bis[3-methoxy-2-hydroxy-propylamino]benzene, 1,4-bis[3-ethoxy-2-hydroxy-propylamino]benzene, 1,4-bis[3-propoxy-2-hydroxy-propylamino]benzene, 1,4-bis[3-butoxy-2-hydroxy-propylamino]benzene, 1,4-bis[3-pentyloxy-2-hydroxy-propylamino]benzene, 1,4-bis[3-hexyloxy-2-hydroxy-propylamino]benzene, 1,4-bis[3-heptyloxy-2-hydroxy-propylamino]benzene, 1,4-bis[3-octyloxy-2-hydroxy-propylamino]benzene, 1,4-bis[3-nonyloxy-2-hydroxy-propylamino]benzene, 1,4-bis[3-decyloxy-2-hydroxy-propylamino]benzene, 1,4-bis[3-undecyloxy-2-hydroxy-propylamino]benzene, 1,4-bis[3-dodecyloxy-2-hydroxy-propylamino]benzene, 1,4-bis[3-tridecyloxy-2-hydroxy-propylamino]benzene, 1,4-bis[3-tetradecyloxy-2-hydroxy-propylamino]benzene, 1,4-bis[3-pentadecyloxy-2-hydroxy-propylamino]benzene, 1,4-bis[3-hexadecyloxy-2-hydroxy-propylamino]benzene, 1,4-bis[(2-heptadecyloxy-2-hydroxy-propylamino]benzene, 1,4-bis[3-octadecyloxy-2-hydroxy-propylamino]benzene, 1,4-bis[3-eleyloxy-2-hydroxy-propylamino]benzene, 1,4-bis[3-nonadecyloxy-2-hydroxy-propylamino]benzene, 1,4-bis[3-eicosyloxy-2-hydroxy-propylamino]benzene, 1,4-bis[3-heneicosyloxy-2-hydroxy propylamino]benzene, 1,4-bis[3-docosyloxy-2-hydroxy-propylamino]benzene, 1,4-bis[3-tricosyloxy-2-hydroxy-propylamino]benzene, and 1,4-bis[3-(2-ethylhexyl)oxy-2-hydroxy-propylamino]benzene.

The anticorrosion compound is selected from the group consisting of: 1,4-bis[bis(3-methoxy-2-hydroxy-propyl)amino]benzene, 1,4-bis[bis(3-ethoxy-2-hydroxy-propyl)amino]benzene, 1,4-bis[bis(3-propoxy-2-hydroxy-propyl)amino]benzene, 1,4-bis[bis(3-butoxy-2-hydroxy-propyl)amino]benzene, 1,4-bis[bis(3-pentyloxy-2-hydroxy-propyl)amino]benzene, 1,4-bis[bis(3-hexyloxy-2-hydroxy-propyl)amino]benzene, 1,4-bis[bis(3-heptyloxy-2-hydroxy-propyl)amino]benzene, 1,4-bis[bis(3-octyloxy-2-hydroxy-propyl)amino]benzene, 1,4-bis[bis(3-nonyloxy-2-hydroxy-propyl)amino]benzene, 1,4-bis[bis(3-decyloxy-2-hydroxy-propyl)amino]benzene, 1,4-bis[bis(3-undecyloxy-2-hydroxy-propyl)amino]benzene, 1,4-bis[bis(3-dodecyloxy-2-hydroxy-propyl)amino]benzene, 1,4-bis[bis(3-tridecyloxy-2-hydroxy-propyl)amino]benzene, 1,4-bis[bis(3-tetradecyloxy-2-hydroxy-propyl)amino]benzene, 1,4-bis[bis(3-pentadecyloxy-2-hydroxy-propyl)amino]benzene, 1,4-bis[bis(3-hexadecyloxy-2-hydroxy-propyl)amino]benzene, 1,4-bis[bis((2-heptadecyloxy-2-hydroxy-propyl)amino]benzene, 1,4-bis[bis(3-octadecyloxy-2-hydroxy-propyl)amino]benzene, 1,4-bis[bis(3-eleyloxy-2-hydroxy-propyl)amino]benzene, 1,4-bis[bis(3-nonadecyloxy-2-hydroxy-propyl)amino]benzene, 1,4-bis[bis(3-eicosyloxy-2-hydroxy-propyl)amino]benzene, 1,4-bis[bis(3-heneicosyloxy-2-hydroxy propyl)amino]benzene, 1,4-bis[bis(3-docosyloxy-2-hydroxy-propyl)amino]benzene, and 1,4-bis[bis(3-tricosyloxy-2-hydroxy-propyl)amino]benzene, 1,4-bis[bis(3-(2-ethylhexyl)oxy-2-hydroxy-propyl)amino]benzene.

The methods described herein, wherein the anticorrosion compound of Formula 1 is present in an amount from about 1 ppm to about 5000 ppm, from about 10 ppm to about 2500 ppm, or from about 50 ppm to about 1500 ppm based on the total weight of the fluid in contact with the surface.

The anti-corrosion compound of Formula 1 can be contained in an anti-corrosion composition that further comprises one or more additional corrosion inhibitors, solvents, asphaltene inhibitors, paraffin inhibitors, scale inhibitors, emulsifiers, water clarifiers, dispersants, emulsion breakers, gas hydrate inhibitors, biocides, pH modifiers, or surfactants.

The anti-corrosion composition described herein comprises from about 0.1 to about 20 wt. % of one or more compounds of formula 1 in a solvent system.

The solvent system can comprise methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The methods described herein can have the surface be part of equipment used in an industrial system. Preferably, the industrial system is a water recirculating system, a cooling water system, a boiler water system, a petroleum well, a downhole formation, a geothermal well, a mineral washing system, a flotation and benefaction system, a papermaking system, a gas scrubber, an air washer, a continuous casting process in the metallurgical industry, an air conditioning and refrigeration system, a water reclamation system, a water purification system, a membrane filtration system, a food processing system, a clarifier system, a municipal sewage treatment system, a municipal water treatment system, or a potable water system.

Also disclosed herein is an anticorrosion composition comprising the anticorrosion compound of Formula 2:

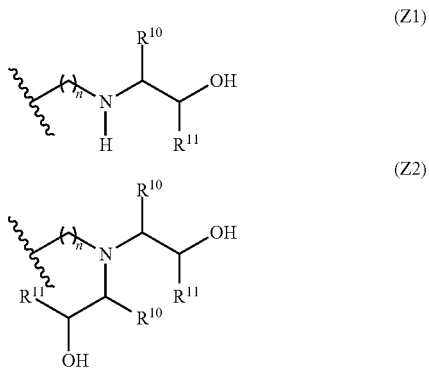

wherein Z has the structure corresponding to Z1 or Z2:

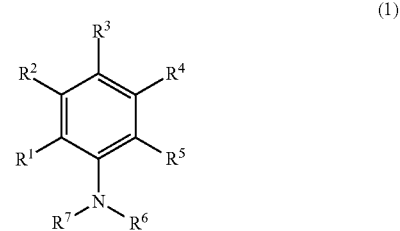

wherein X is hydroxyl, —$NR^8R^9$, or Z; n is an integer from 0 to 10; $R^{10}$ is independently hydrogen, alkyl, or aryl; $R^{11}$ is alkyl, aryl, or —$(CH_2)z$-O—$R^{12}$; $R^{12}$ is hydrogen or alkyl; and z is an integer from 1 to 10; and at least one of an additional corrosion inhibitor, a compound that enhances corrosion performance, an organic solvent, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof, whereby the anticorrosion composition reduces, inhibits, or prevents corrosion of a surface.

The anticorrosion compositions disclosed herein can comprise the compound that enhances corrosion performance, wherein the compound that enhances corrosion performance comprises thioglycolic acid, 3,3'-dithiodipropionic acid, thiosulfate, thiourea, 2-mercaptoethanol, L-cysteine, and ter-butyl mercaptan.

Further, the anticorrosion compositions described herein can have the organic solvent comprise an alcohol, a hydrocarbon, a ketone, an ether, an alkylene glycol, a glycol ether, an amide, a nitrile, a sulfoxide, an ester, or a combination thereof. Preferably, the organic solvent comprises methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

Other objects and features will be in part apparent and in part pointed out hereinafter.

BRIEF DESCRIPTION OF THE SEVERAL VIEWS OF THE DRAWING

FIG. 1 is a graph of corrosion rate versus time showing the results of the bubble tests detailed in Example 6.

DETAILED DESCRIPTION OF THE INVENTION

Disclosed herein are compounds and compositions, methods of using the compounds and compositions for inhibiting corrosion, and processes for their preparation. The compounds and compositions are useful for inhibiting corrosion in industrial systems. The compositions and methods are particularly useful for inhibiting corrosion in equipment used in the production, transportation, storage, and separation of crude oil and natural gas. The compositions include a class of aromatic amine epoxide adduct corrosion inhibitors that are effective and environmentally friendly.

Disclosed herein are methods for reducing, inhibiting, or preventing corrosion of a surface, the method comprising contacting an anticorrosion compound of Formula 1 with the surface, the anticorrosion compound of Formula 1 having a structure corresponding to:

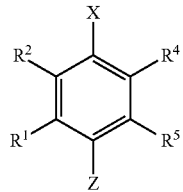

wherein $R^1$, $R^2$, $R^3$, $R^4$, and $R^5$ are independently selected from hydrogen, hydroxyl, alkyl, alkoxyl, aryl, alkaryl, aralkyl, and —$NR^8R^9$; $R^6$ and $R^7$ are independently hydrogen, a substituted alkyl, substituted alkenyl, substituted aryl, substituted alkaryl, or substituted aralkyl, wherein at least one substituent is a hydroxyl or an ether; provided that at least one of $R^6$ and $R^7$ is other than hydrogen; $R^8$ and $R^9$ are independently hydrogen, unsubstituted alkyl, unsubstituted alkenyl, unsubstituted aryl, unsubstituted alkaryl, unsubstituted aralkyl, substituted alkyl, substituted alkenyl, or substituted alkaryl, wherein at least one substituent is a hydroxyl or an ether; or any two adjacent groups of $R^1$, $R^2$, $R^3$, $R^4$, and $R^5$ form one or more ring structures.

The anticorrosion compound of Formula 1 can be added to a fluid in contact with the surface.

In the methods described herein, the surface can comprise a metal.

The substituted alkyl, substituted alkenyl, substituted aryl, substituted alkaryl, or substituted aralkyl of the compound of Formula 1 are substituted with a hydroxyl and an ether group.

For the compounds of Formula 1, at least one of $R^1$, $R^2$, $R^3$, $R^4$, and $R^5$ is hydroxyl or —$NR^8R^9$.

For the compounds of Formula 1, $R^3$ can be hydroxyl; or $R^3$ can be —$NR^8R^9$, wherein $R^8$ is hydrogen and $R^9$ is phenyl or substituted alkyl.

In the methods described herein, the anticorrosion compound of Formula 1 can correspond to the structure of Formula 2:

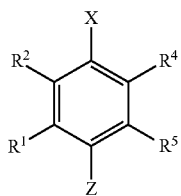

(2)

wherein Z has the structure corresponding to Z1 or Z2:

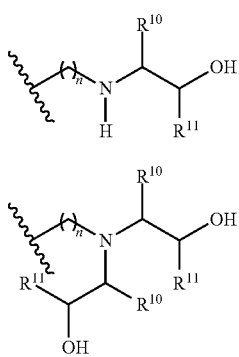

wherein X is hydroxyl, —NR⁸R⁹, or Z; n is an integer from 0 to 10; $R^{10}$ is independently hydrogen, alkyl, or aryl; $R^{11}$ is alkyl, aryl, or —(CH₂)z-O—$R^{12}$; $R^{12}$ is hydrogen or alkyl; and z is an integer from 1 to 10.

The methods can have the compounds of Formula 2, wherein X is hydroxyl.

The compounds of Formula 2 can have X is —NR⁸R⁹, wherein R⁸ is hydrogen and R⁹ is aryl; preferably, X is —NR⁸R⁹, wherein R⁸ is hydrogen and R⁹ is phenyl.

Additionally, the compound of Formula 2 can have X be Z and Z correspond to Z1.

The methods described herein wherein the compound of Formula 2 has n of 0, $R^{10}$ of hydrogen; and $R^{11}$ of (CH₂)z-O—$R^{12}$; preferably, z is 1 and $R^{12}$ is alkyl; more preferably, $R^{12}$ is C₄ to C₁₀ alkyl; most preferably, $R^{12}$ is butyl, pentyl, hexyl, heptyl, or octyl.

The compounds of Formula 2 can have Z be Z1.

The compounds of Formula 2 can also have Z be Z2. For these compounds, n is 0, $R^{10}$ is hydrogen; and $R^{11}$ is —(CH₂)z-O—$R^{12}$; preferably, z is 1 and $R^{12}$ is alkyl; more preferably, $R^{12}$ is C₄ to C₁₀ alkyl; most preferably, $R^{12}$ is butyl, pentyl, hexyl, heptyl, or octyl.

For the methods described herein, the compounds of Formula 1 or 2 can have R¹, R², R⁴, and R⁵ be hydrogen.

In the methods described herein, the anticorrosion compound is selected from the group consisting of: 4-[(2-hydroxyethyl)amino]phenol, 4-[(2-hydroxypropyl)amino]phenol, 4-[(2-hydroxybutyl)amino]phenol, 4-[(2-hydroxypentyl)amino]phenol, 4-[(2-hydroxyhexyl)amino]phenol, 4-[(2-hydroxy-2-phenylethyl)amino]phenol, 4-[(2-hydroxyheptyl)amino]phenol, 4-[(2-hydroxyoctyl)amino]phenol, 4-[(2-hydroxynonyl)amino]phenol, 4-[(2-hydroxydecyl)amino]phenol, 4-[(2-hydroxyundecyl)amino]phenol, 4-[(2-hydroxydodecyl)amino]phenol, 4-[(2-hydroxytridecyl)amino]phenol, 4-[(2-hydroxytetradecyl)amino]phenol, 4-[(2-hydroxypentadecyl)amino]phenol, 4-[(2-hydroxyhexadecyl)amino]phenol, 4-[(2-hydroxyheptadecyl)amino]phenol, 4-[(2-hydroxyoctadecyl)amino]phenol, 4-[(2-hydroxyeleyl)amino]phenol, 4-[(2-hydroxynonadecyl)amino]phenol, 4-[(2-hydroxyeicosyl)amino]phenol, 4-[(2-hydroxyheneicosyl)amino]phenol, 4-[(2-hydroxydocosyl)amino]phenol, and 4-[(2-hydroxytricosyl)amino]phenol.

The anticorrosion compound also can be selected from the group consisting of: 4-[bis(2-hydroxyethyl)amino]phenol, 4-[bis(2-hydroxypropyl)amino]phenol, 4-[bis(2-hydroxybutyl)amino]phenol, 4-[bis(2-hydroxypentyl)amino]phenol, 4-[bis(2-hydroxyhexyl)amino]phenol, 4-[bis(2-hydroxy-2-phenylethyl)amino]phenol, 4-[bis(2-hydroxyheptyl)amino]phenol, 4-[bis(2-hydroxyoctyl)amino]phenol, 4-[bis(2-hydroxynonyl)amino]phenol, 4-[bis(2-hydroxydecyl)amino]phenol, 4-[bis(2-hydroxyundecyl)amino]phenol, 4-[bis(2-hydroxydodecyl)amino]phenol, 4-[bis(2-hydroxytridecyl)amino]phenol, 4-[bis(2-hydroxytetradecyl)amino]phenol, 4-[bis(2-hydroxypentadecyl)amino]phenol, 4-[bis(2-hydroxyhexadecyl)amino]phenol, 4-[bis(2-hydroxyheptadecyl)amino]phenol, 4-[bis(2-hydroxyoctadecyl)amino]phenol, 4-[bis(2-hydroxyeleyl)amino]phenol, 4-[bis(2-hydroxynonadecyl)amino]phenol, 4-[bis(2-hydroxyeicosyl)amino]phenol, 4-[bis(2-hydroxyheneicosyl)amino]phenol, and 4-[bis(2-hydroxydocosyl)amino]phenol.

The anticorrosion compound can further be selected from the group consisting of: 4-[(methoxymethyl)amino]phenol, 4-[(2-methoxyethyl)amino]phenol, 4-[(3-methoxypropyl)amino]phenol, 4-[(4-methoxybutyl)amino]phenol, 4-[(5-methoxypentyl)amino]phenol, 4-[(6-methoxyhexyl)amino]phenol, 4-[(methoxyphenyl)amino]phenol, 4-[(ethoxymethyl)amino]phenol, 4-[(2-ethoxyethyl)amino]phenol, 4-[(3-ethoxypropyl)amino]phenol, 4-[(4-ethoxybutyl)amino]phenol, 4-[(5-ethoxypentyl)amino]phenol, 4-[(6-ethoxyhexyl)amino]phenol, 4-[(ethoxyphenyl)amino]phenol, 4-[(propoxymethyl)amino]phenol, 4-[(2-propoxyethyl)amino]phenol, 4-[(3-propoxypropyl)amino]phenol, 4-[(4-propoxybutyl)amino]phenol, 4-[(5-propoxypentyl)amino]phenol, 4-[(6-propoxyhexyl)amino]phenol, 4-[(propoxyphenyl)amino]phenol, 4-[(butoxymethyl)amino]phenol, 4-[(2-butoxyethyl)amino]phenol, 4-[(3-butoxypropyl)amino]phenol, 4-[(4-butoxybutyl)amino]phenol, 4-[(5-butoxypentyl)amino]phenol, 4-[(6-butoxyhexyl)amino]phenol, and 4-[(butoxyphenyl)amino]phenol.

The anticorrosion compound can be selected from the group consisting of: 4-[bis(methoxymethyl)amino]phenol, 4-[bis(2-methoxyethyl)amino]phenol, 4-[bis(3-methoxypropyl)amino]phenol, 4-[bis(4-methoxybutyl)amino]phenol, 4-[bis(5-methoxypentyl)amino]phenol, 4-[bis(6-methoxyhexyl)amino]phenol, 4-[bis(methoxyphenyl)amino]phenol, 4-[bis(ethoxymethyl)amino]phenol, 4-[bis(2-ethoxyethyl)amino]phenol, 4-[bis(3-ethoxypropyl)amino]phenol, 4-[bis(4-ethoxybutyl)amino]phenol, 4-[bis(5-ethoxypentyl)amino]phenol, 4-[bis(6-ethoxyhexyl)amino]phenol, 4-[bis(ethoxyphenyl)amino]phenol, 4-[bis(propoxymethyl)amino]phenol, 4-[bis(2-propoxyethyl)amino]phenol, 4-[bis(3-propoxypropyl)amino]phenol, 4-[bis(4-propoxybutyl)amino]phenol, 4-[bis(5-propoxypentyl)amino]phenol, 4-[bis(6-propoxyhexyl)amino]phenol, 4-[bis(propoxyphenyl)amino]phenol, 4-[bis(butoxymethyl)amino]phenol, 4-[bis(2-butoxyethyl)amino]phenol, 4-[bis(3-butoxypropyl)amino]phenol, 4-[bis(4-butoxybutyl)amino]phenol, 4-[bis(5-butoxypentyl)amino]phenol, 4-[bis(6-butoxyhexyl)amino]phenol, and 4-[bis(butoxyphenyl)amino]phenol.

The anticorrosion compound can also be selected from the group consisting of: 4-[(3-methoxy-2-hydroxy-propyl)amino]phenol, 4-[(3-ethoxy-2-hydroxy-propyl)amino]phenol, 4-[(3-propoxy-2-hydroxy-propyl)amino]phenol, 4-[(3-butoxy-2-hydroxy-propyl)amino]phenol, 4-[(3-pentyloxy- 2-hydroxy-propyl)amino]phenol, 4-[(3-hexyloxy-2-hydroxy-propyl)amino]phenol, 4-[(3-heptyloxy-2-hydroxy-propyl)amino]phenol, 4-[(3-octyloxy-2-hydroxy-propyl)amino]phenol, 4-[(3-nonyloxy-2-hydroxy-propyl)amino]phenol, 4-[(3-decyloxy-2-hydroxy-propyl)amino]phenol, 4-[(3-undecyloxy-2-hydroxy-propyl)amino]phenol, 4-[(3-dodecyloxy-2-hydroxy-propyl)amino]phenol, 4-[(3-tridecyloxy-2-hydroxy-propyl)amino]phenol, 4-[(3-tetradecyloxy-2-hydroxy-propyl)amino]phenol, 4-[(3-pentadecyloxy-2-hydroxy-propyl)amino]phenol, 4-[(3-hexadecyloxy-2-hydroxy-propyl)amino]phenol, 4-[(3-heptadecyloxy-2-hydroxy-propyl)amino]phenol, 4-[(3-octadecyloxy-2-hydroxy-propyl)amino]phenol, 4-[(3-eleyloxy-2-hydroxy-propyl)amino]phenol, 4-[(3-nonadecyloxy-2-hydroxy-propyl)amino]phenol, 4-[(3-eicosyloxy-2-hydroxy-propyl)amino]phenol, 4-[(3-heneicosyloxy-2-hydroxy-propyl)amino]phenol, 4-[(3-docosyloxy-2-hydroxy-propyl)amino]phenol, 4-[(3-tricosyloxy-2-hydroxy-propyl)amino]phenol, and 4-[bis(3-(2-ethylhexyl)oxy-2-hydroxy-propyl)amino]phenol.

The anticorrosion compound is additionally selected from the group consisting of: 4-[bis(3-methoxy-2-hydroxy-propyl)amino]phenol, 4-[bis(3-ethoxy-2-hydroxy-propyl)amino]phenol, 4-[bis(3-propoxy-2-hydroxy-propyl)amino]phenol, 4-[bis(3-butoxy-2-hydroxy-propyl)amino]phenol, 4-[bis(3-pentyloxy-2-hydroxy-propyl)amino]phenol, 4-[bis(3-hexyloxy-2-hydroxy-propyl)amino]phenol, 4-[bis(3-heptyloxy-2-hydroxy-propyl)amino]phenol, 4-[bis(3-octyloxy-2-hydroxy-propyl)amino]phenol, 4-[bis(3-nonyloxy-2-hydroxy-propyl)amino]phenol, 4-[bis(3-decyloxy-2-hydroxy-propyl)amino]phenol, 4-[bis(3-undecyloxy-2-hydroxy-propyl)amino]phenol, 4-[bis(3-dodecyloxy-2-hydroxy-propyl)amino]phenol, 4-[bis(3-tridecyloxy-2-hydroxy-propyl)amino]phenol, 4-[bis(3-tetradecyloxy-2-hydroxy-propyl)amino]phenol, 4-[bis(3-pentadecyloxy-2-hydroxy-propyl)amino]phenol, 4-[bis(3-hexadecyloxy-2-hydroxy-propyl)amino]phenol, 4-[bis(3-heptadecyloxy-2-hydroxy-propyl)amino]phenol, 4-[bis(3-octadecyloxy-2-hydroxy-propyl)amino]phenol, 4-[bis(3-eleyloxy-2-hydroxy-propyl)amino]phenol, 4-[bis(3-nonadecyloxy-2-hydroxy-propyl)amino]phenol, 4-[bis(3-eicosyloxy-2-hydroxy-propyl)amino]phenol, 4-[bis(3-heneicosyloxy-2-hydroxy-propyl)amino]phenol, 4-[bis(3-docosyloxy-2-hydroxy-propyl)amino]phenol, 4-[bis(3-tricosyloxy-2-hydroxy-propyl)amino]phenol, and 4-[bis(3-(2-ethylhexyl)oxy-2-hydroxy-propyl)amino]phenol.

The anticorrosion compound is also selected from the group consisting of: 1,4-bis[3-methoxy-2-hydroxy-propylamino]benzene, 1,4-bis[3-ethoxy-2-hydroxy-propylamino]benzene, 1,4-bis[3-propoxy-2-hydroxy-propylamino]benzene, 1,4-bis[3-butoxy-2-hydroxy-propylamino]benzene, 1,4-bis[3-pentyloxy-2-hydroxy-propylamino]benzene, 1,4-bis[3-hexyloxy-2-hydroxy-propylamino]benzene, 1,4-bis[3-heptyloxy-2-hydroxy-propylamino]benzene, 1,4-bis[3-octyloxy-2-hydroxy-propylamino]benzene, 1,4-bis[3-nonyloxy-2-hydroxy-propylamino]benzene, 1,4-bis[3-decyloxy-2-hydroxy-propylamino]benzene, 1,4-bis[3-undecyloxy-2-hydroxy-propylamino]benzene, 1,4-bis[3-dodecyloxy-2-hydroxy-propylamino]benzene, 1,4-bis[3-tridecyloxy-2-hydroxy-propylamino]benzene, 1,4-bis[3-tetradecyloxy-2-hydroxy-propylamino]benzene, 1,4-bis[3-pentadecyloxy-2-hydroxy-propylamino]benzene, 1,4-bis[3-hexadecyloxy-2-hydroxy-propylamino]benzene, 1,4-bis[(2-heptadecyloxy-2-hydroxy-propylamino]benzene, 1,4-bis[3-octadecyloxy-2-hydroxy-propylamino]benzene, 1,4-bis[3-eleyloxy-2-hydroxy-propylamino]benzene, 1,4-bis[3-nonadecyloxy-2-hydroxy-propylamino]benzene, 1,4-bis[3-eicosyloxy-2-hydroxy-propylamino]benzene, 1,4-bis[3-heneicosyloxy-2-hydroxy propylamino]benzene, 1,4-bis[3-docosyloxy-2-hydroxy-propylamino]benzene, 1,4-bis[3-tricosyloxy-2-hydroxy-propylamino]benzene, and 1,4-bis[3-(2-ethylhexyl)oxy-2-hydroxy-propylamino]benzene.

The anticorrosion compound is selected from the group consisting of: 1,4-bis[bis(3-methoxy-2-hydroxy-propyl)amino]benzene, 1,4-bis[bis(3-ethoxy-2-hydroxy-propyl)amino]benzene, 1,4-bis[bis(3-propoxy-2-hydroxy-propyl)amino]benzene, 1,4-bis[bis(3-butoxy-2-hydroxy-propyl)amino]benzene, 1,4-bis[bis(3-pentyloxy-2-hydroxy-propyl)amino]benzene, 1,4-bis[bis(3-hexyloxy-2-hydroxy-propyl)amino]benzene, 1,4-bis[bis(3-heptyloxy-2-hydroxy-propyl)amino]benzene, 1,4-bis[bis(3-octyloxy-2-hydroxy-propyl)amino]benzene, 1,4-bis[bis(3-nonyloxy-2-hydroxy-propyl)amino]benzene, 1,4-bis[bis(3-decyloxy-2-hydroxy-propyl)amino]benzene, 1,4-bis[bis(3-undecyloxy-2-hydroxy-propyl)amino]benzene, 1,4-bis[bis(3-dodecyloxy-2-hydroxy-propyl)amino]benzene, 1,4-bis[bis(3-tridecyloxy-2-hydroxy-propyl)amino]benzene, 1,4-bis[bis(3-tetradecyloxy-2-hydroxy-propyl)amino]benzene, 1,4-bis[bis(3-pentadecyloxy-2-hydroxy-propyl)amino]benzene, 1,4-bis[bis(3-hexadecyloxy-2-hydroxy-propyl)amino]benzene, 1,4-bis[bis((2-heptadecyloxy-2-hydroxy-propyl)amino]benzene, 1,4-bis[bis(3-octadecyloxy-2-hydroxy-propyl)amino]benzene, 1,4-bis[bis(3-eleyloxy-2-hydroxy-propyl)amino]benzene, 1,4-bis[bis(3-nonadecyloxy-2-hydroxy-propyl)amino]benzene, 1,4-bis[bis(3-eicosyloxy-2-hydroxy-propyl)amino]benzene, 1,4-bis[bis(3-heneicosyloxy-2-hydroxy propyl)amino]benzene, 1,4-bis[bis(3-docosyloxy-2-hydroxy-propyl)amino]benzene, and 1,4-bis[bis(3-tricosyloxy-2-hydroxy-propyl)amino]benzene, 1,4-bis[bis(3-(2-ethylhexyl)oxy-2-hydroxy-propyl)amino]benzene.

In particular, the anticorrosion compound can be selected from

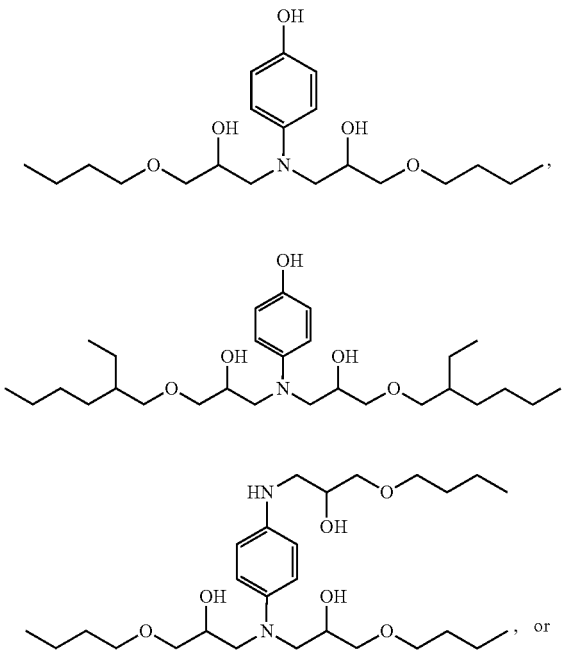

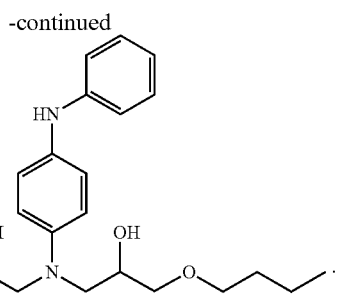

The anticorrosion compounds of Formula 1 or 2 can be prepared using the following reaction scheme.

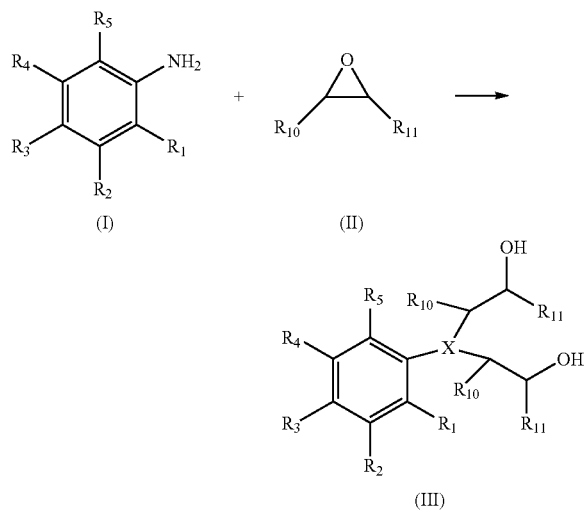

wherein $R^1$, $R^2$, $R^3$, $R^4$, and $R^5$ are independently selected from hydrogen, hydroxyl, alkyl, aryl, alkaryl, aralkyl, and —$NR^8R^9$; $R^8$ and $R^9$ are independently hydrogen, unsubstituted alkyl, unsubstituted alkenyl, unsubstituted aryl, unsubstituted alkaryl, unsubstituted aralkyl, substituted alkyl, substituted alkenyl, or substituted alkaryl, wherein at least one substituent is a hydroxyl or an ether; $R^{10}$ is independently hydrogen, alkyl, or aryl; $R^{11}$ is alkyl, aryl, or —$(CH_2)z$-O—$R^{12}$; $R^{12}$ is hydrogen or alkyl; and z is an integer from 1 to 10.

For the methods described herein, the anticorrosion compound of Formula 1 can be present in an amount from about 0.11 ppm to about 10000 ppm, from about 0.1 ppm to about 5000 ppm, from about 0.1 ppm to about 3000 ppm, from about 0.1 ppm to about 2000 ppm, from about 0.1 ppm to about 1500 ppm, from about 0.1 ppm to about 1000 ppm, from about 0.1 ppm to about 500 ppm, from about 0.5 ppm to about 5000 ppm, from about 0.5 ppm to about 4000 ppm, from about 0.5 ppm to about 3000 ppm, from about 0.5 ppm to about 2500 ppm, from about 0.5 ppm to about 2000 ppm, from about 0.5 ppm to about 1500 ppm, from about 0.5 ppm to about 1000 ppm, from about 0.5 ppm to about 500 ppm, from about 1 ppm to about 5000 ppm, from about 1 ppm to about 4000 ppm, from about 1 ppm to about 3000 ppm, from about 1 ppm to about 2500 ppm, from about 1 ppm to about 2000 ppm, from about 1 ppm to about 1500 ppm, from about 1 ppm to about 1000 ppm, from about 1 ppm to about 500 ppm, from about 1 ppm to about 100 ppm, or from about 1 ppm to about 10 ppm, based on the total weight of the fluid in contact with the surface.

The anti-corrosion compound of Formula 1 can be contained in an anti-corrosion composition that further comprises one or more additional corrosion inhibitors, an organic solvent, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

The anti-corrosion composition described herein comprises from about 0.1 to about 20 wt. % of one or more compounds of formula 1 in a solvent system.

The organic solvent can comprise an alcohol, a hydrocarbon, a ketone, an ether, an alkylene glycol, a glycol ether, an amide, a nitrile, a sulfoxide, an ester, or any combination thereof, and the composition optionally comprises water.

Preferably, the organic solvent comprises methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

A compound used to enhance the corrosion performance of the composition can also be included in the anticorrosion composition. For example, thioglycolic acid, 3,3'-dithiopropioinic acid, thiosulfate, thiourea, 2-mercaptoethanol, L-cysteine, tert-butyl mercaptan, or a combination thereof can be included in the anticorrosion composition.

The methods described herein can have the surface be part of equipment used in an industrial system. Preferably, the industrial system is a water recirculating system, a cooling water system, a boiler water system, a pulp slurry, a papermaking process, a ceramic slurry, a mixed solid/liquid system, or an oil-field system.

The methods can have the surface be part of equipment used in the production, transportation, storage, and/or separation of crude oil or natural gas. Preferably, the equipment comprises a pipeline, a storage vessel, downhole injection tubing, a flow line, or an injection line.

The methods described herein can have the fluid be used in the operation of the industrial system.

The fluid can comprise seawater, produced water, fresh water, brackish water, drilling fluid, completion fluid, or a combination thereof.

Further disclosed is a composition for inhibiting corrosion at a surface. The composition comprises an effective amount of the compound of formula 1 or 2 and a component comprising an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

The composition can comprise, for example, from about 0.1 to about 20 wt. % of one or more compounds of formula (1) and from about 80 to about 99.9 wt. % of the component; from about 0.1 to about 20 wt. % of one or more compounds of formula (1), from about 1 to about 60 wt. % of the component and from about 20 to about 98.9 wt. % water; from about 10 to about 20 wt. % of one or more compounds of formula (1), from about 30 to about 40 wt. % of the component and from about 40 to about 60 wt. % water; or from about 15 to about 20 wt. % of one or more compounds of formula (1), from about 1 to about 10 wt. % of the component and from about 70 to about 84 wt. % water.

The component of the composition can comprise an organic solvent. The composition can comprise from about 1 to 80 wt. %, from about 5 to 50 wt. %, or from about 10 to 35 wt. % of the one or more organic solvents, based on total weight of the composition. The organic solvent can comprise an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

In addition to the component, the composition can comprise water.

The component of the composition can comprise a corrosion inhibitor in addition to the one or more compounds of formula (1). The composition can comprise from about 0.1 to 20 wt. %, 0.1 to 10 wt. %, or 0.1 to 5 wt. % of the one or more additional corrosion inhibitors, based on total weight of the composition. A composition can comprise from 0 to 10 percent by weight of the one or more additional corrosion inhibitors, based on total weight of the composition. The composition can comprise 1.0 wt. %, 1.5 wt. %, 2.0 wt. %, 2.5 wt. %, 3.0 wt. %, 3.5 wt. %, 4.0 wt. %, 4.5 wt. %, 5.0 wt. %, 5.5 wt. %, 6.0 wt. %, 6.5 wt. %, 7.0 wt. %, 7.5 wt. %, 8.0 wt. %, 8.5 wt. %, 9.0 wt. %, 9.5 wt. %, 10.0 wt. %, 10.5 wt. %, 11.0 wt. %, 11.5 wt. %, 12.0 wt. %, 12.5 wt. %, 13.0 wt. %, 13.5 wt. %, 14.0 wt. %, 14.5 wt. %, or 15.0 wt. % by weight of the one or more additional corrosion inhibitors, based on total weight of the composition. Each system can have its own requirements, and the weight percent of one or more additional corrosion inhibitors in the composition can vary with the system in which it is used.

The one or more additional corrosion inhibitors can comprise an imidazoline compound, a quaternary ammonium compound, a pyridinium compound, or a combination thereof.

The one or more additional corrosion inhibitor component can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (I) or an imidazoline derivative. Representative imidazoline derivatives include an imidazolinium compound of Formula (II) or a bis-quaternized compound of Formula (III).

The one or more additional corrosion inhibitor component can include an imidazoline of Formula (I):

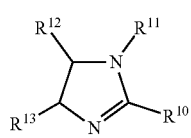

(I)

wherein $R^{10}$ is a $C_1$-$C_{20}$ alkyl or a $C_1$-$C_{20}$ alkoxyalkyl group; $R^{11}$ is hydrogen, $C_1$-$C_6$ alkyl, $C_1$-$C_6$ hydroxyalkyl, or $C_1$-$C_6$ arylalkyl; and $R^{12}$ and $R^{13}$ are independently hydrogen or a $C_1$-$C_6$ alkyl group. Preferably, the imidazoline includes an $R^{10}$ which is the alkyl mixture typical in tall oil fatty acid (TOFA), and $R^{11}$, $R^{12}$ and $R^{13}$ are each hydrogen.

The one or more additional corrosion inhibitor component can include an imidazolinium compound of Formula (II):

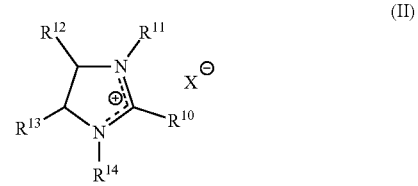

(II)

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The one or more additional corrosion inhibitors can comprise a bis-quaternized compound having the formula (III):

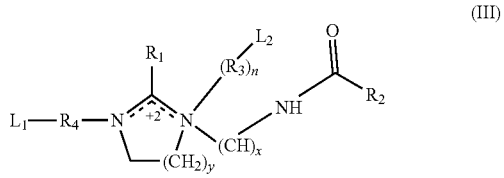

(III)

wherein:
 $R_1$ and $R_2$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof;
 $R_3$ and $R_4$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof;
 $L_1$ and $L_2$ are each independently absent, H, —COOH, —SO$_3$H, —PO$_3$H$_2$, —COOR$_5$, —CONH$_2$, —CONHR$_5$, or —CON(R$_5$)$_2$;
 $R_5$ is each independently a branched or unbranched alkyl, aryl, alkylaryl, alkylheteroaryl, cycloalkyl, or heteroaryl group having from 1 to about 10 carbon atoms;
 n is 0 or 1, and when n is 0, $L_2$ is absent or H;
 x is from 1 to about 10; and
 y is from 1 to about 5. Preferably, $R_1$ and $R_2$ are each independently $C_6$-$C_{22}$ alkyl, $C_8$-$C_{20}$) alkyl, $C_{12}$-$C_{18}$ alkyl, $C_{16}$-$C_{18}$ alkyl, or a combination thereof; $R_3$ and $R_4$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1;

$R_3$ and $R_4$ are —$C_2H_2$—; $L_1$ is —COOH, —$SO_3H$, or —$PO_3H_2$; and $L_2$ is absent, H, —COOH, —$SO_3H$, or —$PO_3H_2$. For example, $R_1$ and $R_2$ can be derived from a mixture of tall oil fatty acids and are predominantly a mixture of $C_{17}H_{33}$ and $C_{17}H_{31}$ or can be $C_{16}$-$C_{18}$ alkyl; $R_3$ and $R_4$ can be $C_2$-$C_3$ alkylene such as —$C_2H_2$—; n is 1 and $L_2$ is —COOH or n is 0 and $L_2$ is absent or H; x is 2; y is 1; $R_3$ and $R_4$ are —$C_2H_2$—; and $L_1$ is —COOH.

It should be appreciated that the number of carbon atoms specified for each group of formula (III) refers to the main chain of carbon atoms and does not include carbon atoms that may be contributed by substituents.

The one or more additional corrosion inhibitors can comprise a bis-quaternized imidazoline compound having the formula (III) wherein $R_1$ and $R_2$ are each independently $C_6$-$C_{22}$ alkyl, $C_8$-$C_{20}$ alkyl, $C_{12}$-$C_{18}$ alkyl, or $C_{16}$-$C_{18}$ alkyl or a combination thereof; $R_4$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —$SO_3H$, or —$PO_3H_2$; and $L_2$ is absent or H. Preferably, a bis-quaternized compound has the formula (III) wherein $R_1$ and $R_2$ are each independently $C_{16}$-$C_{18}$ alkyl; $R_4$ is —$C_2H_2$—; x is 2; y is 1; n is 0; $L_1$ is —COOH, —$SO_3H$, or —$PO_3H_2$ and $L_2$ is absent or H.

The one or more additional corrosion inhibitors can be a quaternary ammonium compound of Formula (IV):

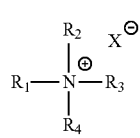

(IV)

wherein $R_1$, $R_2$, and $R_3$ are independently $C_1$ to $C_{20}$ alkyl, $R_4$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula $[N^+R^{5a}R^{6a}R^{7a}R^{8a}][X^-]$ wherein $R^{5a}$, $R^{6a}$, $R^{7a}$, and $R^{8a}$ contain one to 18 carbon atoms, and X is Cl, Br or I. For the quaternary salts, $R^{5a}$, $R^{6a}$, $R^{7a}$, and $R^{8a}$ can each be independently alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula $[N^+R^{5a}R^{6a}R^{7a}R^{8a}][X^-]$ wherein $R^{5a}$, $R^{6a}$, $R^{7a}$, and $R^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The one or more additional corrosion inhibitor component can comprise a pyridinium salt such as those represented by Formula (V):

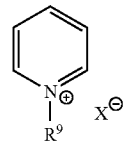

(V)

wherein $R^9$ is an alkyl group, an aryl group, or an arylalkyl group, wherein said alkyl groups have from 1 to about 18 carbon atoms and $X^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The one or more additional corrosion inhibitor components can include additional corrosion inhibitors such as phosphate esters, monomeric or oligomeric fatty acids, or alkoxylated amines.

The one or more additional corrosion inhibitor component can comprise a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The one or more additional corrosion inhibitor component can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The one or more additional corrosion inhibitor component can comprise an alkoxylated amine. The alkoxylated amine can be an ethoxylated alkyl amine. The alkoxylated amine can be ethoxylated tallow amine.

The component of the composition can comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. The organic sulfur compound can constitute 0.5 to 15 wt. % of the composition, based on total weight of the composition, preferably about 1 to about 10 wt. % and more preferably about 1 to about 5 wt. %. The organic sulfur compound can constitute 1, 2, 3, 4, 5, 6, 7, 8, 9, 10, 11, 12, 13, 14 or 15 wt. % of the composition.

The composition can be substantially free of or free of any organic sulfur compound other than the compound of formula (1). A composition is substantially free of any organic sulfur compound if it contains an amount of organic sulfur compound less than 0.50 wt. % preferably less than 0.10 wt. %, and more preferably less than 0.01 wt. %.

The component of the composition can further include a demulsifier. Preferably, the demulsifier comprises an oxyalkylate polymer, such as a polyalkylene glycol. The demulsifier can constitute from about 0.1 to 10 wt. %, from about 0.5 to 5 wt. %, or from about 0.5 to 4 wt. % of the composition, based on total weight of the composition. The demulsifier can constitute 0.5, 1, 1.5, 2, 2.5, 3, 3.5, 4, 4.5 or 5 wt. % of the composition.

The component of the composition can include an asphaltene inhibitor. The composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The component of the composition can include a paraffin inhibitor. The composition can comprise from about 0.1 to 10 wt. %, from about 0.1 to 5 wt. %, or from about 0.5 to 4 wt. % of a paraffin inhibitor, based on total weight of the composition. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The component of the composition can include a scale inhibitor. The composition can comprise from about 0.1 to 20 wt. %, from about 0.5 to 10 wt. %, or from about 1 to 10 wt. % of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The component of the composition can include an emulsifier. The composition can comprise from about 0.1 to 10 wt. %, from about 0.5 to 5 wt. %, or from about 0.5 to 4 wt. % of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

The component of the composition can include a water clarifier. The composition can comprise from about 0.1 to 10 wt. %, from about 0.5 to 5 wt. %, or from about 0.5 to 4 wt. % of a water clarifier, based on total weight of the composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The component of the composition can include a dispersant. The composition can comprise from about 0.1 to 10 wt. %, from about 0.5 to 5 wt. %, or from about 0.5 to 4 wt. % of a dispersant, based on total weight of the composition. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The component of the composition can include an emulsion breaker. The composition can comprise from about 0.1 to 10 wt. %, from about 0.5 to 5 wt. %, or from about 0.5 to 4 wt. % of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and nonionic surfactants, and resins, such as phenolic and epoxide resins.

The component of the composition can include a hydrogen sulfide scavenger. The composition can comprise from about 1 to 50 wt. %, from about 1 to 40 wt. %, or from about 1 to 30 wt. % of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The component of the composition can include a gas hydrate inhibitor. The composition can comprise from about 0.1 to 25 wt. %, from about 0.5 to 20 wt. %, or from about 1 to 10 wt. % of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The component of the composition can include a kinetic hydrate inhibitor. The composition can comprise from about 0.1 to 25 wt. %, from about 0.5 to 20 wt. %, or from about 1 to 10 wt. % of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The component of the composition can include a biocide. The composition can comprise from about 0.1 to 10 wt. %, from about 0.5 to 5 wt. %, or from about 0.5 to 4 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

The component of the composition can include a pH modifier. The composition can comprise from about 0.1 to 20 wt. %, from about 0.5 to 10 wt. %, or from about 0.5 to 5 wt. % of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The component of the composition can include a surfactant. The composition can comprise from about 0.1 to 10 wt. %, from about 0.5 to 5 wt. %, or from about 0.5 to 4 wt. % of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

Corrosion inhibitor compositions disclosed herein can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the compositions can not contain any of the additional agents or additives.

Additionally, the corrosion inhibitors can be formulated into compositions comprising the following components. These formulations include the ranges of the components listed and can optionally include additional agents.

| Component | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| Compound of Formula 1 or 2 | 0.1-20 | 0.1-20 | 0.1-20 | 0.1-20 | 0.1-20 | 0.1-20 | 10-20 | 10-20 | 10-20 | 10-20 | 10-20 | 0.1-20 |
| Organic solvent | 5-40 | — | 5-50 | — | 5-50 | 5-50 | 5-40 | — | 5-50 | — | — | 10-20 |
| Additional corrosion inhibitor | 0.1-20 | 0.1-20 | — | — | — | — | 0.1-20 | 0.1-20 | — | — | — | 0.1-20 |
| Asphaltene inhibitor | 0.1-5 | 0.1-5 | 0.1-5 | 0.1-5 | — | — | 0.1-5 | 0.1-5 | 0.1-5 | — | — | 0.1-5 |
| Scale inhibitor | 1-10 | 1-10 | 1-10 | 1-10 | 1-10 | — | 1-10 | 1-10 | 1-10 | 1-10 | — | 1-10 |
| Gas hydrate inhibitor | — | — | — | — | — | — | — | — | — | — | — | 0.1-25 |

-continued

| | | | | | | | | | | | |
|---|---|---|---|---|---|---|---|---|---|---|---|
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 |
| Water | 0.00 | 0-40 | 0-10 | 0-60 | 0-15 | 0-25 | 0.00 | 0-40 | 0-10 | 0-65 | 0-75 |

| Component | 13 | 14 | 15 | 16 | 17 | 18 | 19 | 20 | 21 | 22 | 23 | 24 |
|---|---|---|---|---|---|---|---|---|---|---|---|---|
| Compound of Formula 1 or 2 | 0.1-20 | 0.1-20 | 0.1-20 | 0.1-20 | 0.1-20 | 0.1-20 | 10-20 | 10-20 | 10-20 | 10-20 | 10-20 | 10-20 |
| Organic solvent | — | 10-20 | — | 10-35 | 10-35 | — | 10-15 | — | — | 10-35 | 10-35 | — |
| Additional corrosion inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Asphaltene inhibitor | 0.1-5 | — | — | — | — | — | 0.1-5 | — | — | — | — | — |
| Scale inhibitor | 1-10 | 1-10 | — | — | 1-10 | — | 1-10 | 1-10 | — | — | — | 1-10 |
| Gas hydrate inhibitor | 0.1-25 | 0.1-25 | 0.1-25 | — | — | — | 0.1-25 | 0.1-25 | 0.1-25 | — | 0.1-25 | — |
| Biocide | — | — | — | — | — | 0.5-5 | 0.5-5 | 0.5-5 | 0.5-5 | 0.5-5 | — | — |
| Water | 0-20 | 0-5 | 0-35 | 0-25 | 0-15 | 0-55 | 0.00 | 0-20 | 0-30 | 0-20 | 0.00 | 0-50 |

Also disclosed is a method of inhibiting corrosion at a surface. The method comprises either: contacting the surface with an effective amount of a compound of formula (1) to inhibit corrosion on the surface; contacting the surface with a composition comprising an effective amount of the compound of formula (1) and a component comprising an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof to inhibit corrosion on the surface; or adding the compound or the composition to a fluid which contacts the surface to inhibit corrosion on the surface. The composition can be any composition as described herein.

The compounds/compositions can be used for inhibiting corrosion in oil and gas applications such as by treating a gas or liquid stream with an effective amount of a compound or composition as described herein. The compounds and compositions can be used in any industry where it is desirable to inhibit corrosion at a surface.

The compounds/compositions can be used in water systems, condensate/oil systems/gas systems, or any combination thereof. For example, the compounds/compositions can be used in controlling scale on heat exchanger surfaces.

The compounds/compositions can be applied to a gas or liquid produced, or used in the production, transportation, storage, and/or separation of crude oil or natural gas.

The compounds/compositions can be applied to a gas stream used or produced in a coal-fired process, such as a coal-fired power plant.

The compounds/compositions can be applied to a gas or liquid produced or used in a waste-water process, a farm, a slaughter house, a land-fill, a municipality waste-water plant, a coking coal process, or a biofuel process.

A fluid to which the compounds/compositions can be introduced can be an aqueous medium. The aqueous medium can comprise water, gas, and optionally liquid hydrocarbon.

A fluid to which the compounds/compositions can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene.

The fluid or gas can be a refined hydrocarbon product.

A fluid or gas treated with a compound/composition can be at any selected temperature, such as ambient temperature or an elevated temperature. The fluid (e.g., liquid hydrocarbon) or gas can be at a temperature of from about 40° C. to about 250° C. The fluid or gas can be at a temperature of from −50° C. to 300° C., 0° C. to 200° C., 10° C. to 100° C., or 20° C. to 90° C. The fluid or gas can be at a temperature of 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. The fluid or gas can be at a temperature of 85° C., 86° C., 87° C., 88° C., 89° C., 90° C., 91° C., 92° C., 93° C., 94° C., 95° C., 96° C., 97° C., 98° C., 99° C., or 100° C.

The compounds/compositions can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas in which the compounds/compositions are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units.

The compounds/compositions can be introduced into a fluid or gas by any appropriate method for ensuring dispersal through the fluid or gas.

The compounds/compositions can be added to the hydrocarbon fluid before the hydrocarbon fluid contacts the surface.

The compounds/compositions can be added at a point in a flow line upstream from the point at which corrosion prevention is desired.

The compounds/compositions can be injected using mechanical equipment such as chemical injection pumps, piping tees, injection fittings, atomizers, quills, and the like.

The compounds/compositions disclosed can be introduced with or without one or more additional polar or non-polar solvents depending upon the application and requirements.

The compounds/compositions can be pumped into an oil and/or gas pipeline using an umbilical line. A capillary injection system can be used to deliver the compounds/compositions to a selected fluid.

The compounds/compositions can be introduced into a liquid and mixed.

The compounds/compositions can be injected into a gas stream as an aqueous or non-aqueous solution, mixture, or slurry.

The fluid or gas can be passed through an absorption tower comprising compounds/compositions.

The compounds/compositions can be applied continuously, in batch, or a combination thereof. The compounds/compositions doses can be continuous to prevent corrosion. The compounds/compositions doses can be intermittent (i.e., batch treatment) or the compounds/compositions doses can be continuous/maintained and/or intermittent to inhibit corrosion.

The flow rate of a flow line in which the compound/composition is used can be between 0 and 100 feet per second, or between 0.1 and 50 feet per second. The compounds/compositions can also be formulated with water in order to facilitate addition to the flow line.

The compounds/compositions can be used for inhibiting corrosion in other applications.

The compounds/compositions are useful for corrosion inhibition of containers, processing facilities, or equipment in the food service or food processing industries. The compounds/compositions have particular value for use on food packaging materials and equipment, and especially for cold or hot aseptic packaging. Examples of process facilities in which the compounds/compositions can be employed include a milk line dairy, a continuous brewing system, food processing lines such as pumpable food systems and beverage lines, ware wash machines, low temperature ware wash machines, dishware, bottle washers, bottle chillers, warmers, third sink washers, processing equipment such as tanks, vats, lines, pumps and hoses (e.g., dairy processing equipment for processing milk, cheese, ice cream and other dairy products), and transportation vehicles. The compounds/compositions can be used to inhibit corrosion in tanks, lines, pumps, and other equipment used for the manufacture and storage of soft drink materials, and also used in the bottling or containers for the beverages.

The compounds/compositions can also be used on or in other industrial equipment and in other industrial process streams such as heaters, cooling towers, boilers, retort waters, rinse waters, aseptic packaging wash waters, and the like. The compounds/compositions can be used to treat surfaces in recreational waters such as in pools, spas, recreational flumes and water slides, fountains, and the like.

The compounds/compositions can be used to inhibit the corrosion of metal surfaces contacted with cleaners in surfaces found in janitorial and/or housekeeping applications, food processing equipment and/or plant applications, and in laundry applications. For example, the corrosion of washers, such as tunnel washers for washing textiles, can be inhibited according to methods disclosed herein.

The compounds/compositions can be used or applied in combination with low temperature dish and/or warewash sanitizing final rinse, toilet bowl cleaners, and laundry bleaches. The compounds, compositions and methods can be used to treat metal surfaces, such as ware, cleaned and/or sanitized with corrosive sources.

The compounds, compositions and methods disclosed herein protect surfaces from corrosion caused by hypochlorite bleach. A method can include providing the corrosion inhibitor compounds/compositions to a surface treated with a hypochlorite solution in order to inhibit corrosion caused by the hypochlorite solution. The method can include preparing an aqueous use composition of the present corrosion inhibitor composition. The method can further include contacting a surface, such as a hard metal surface, in need of corrosion inhibition due to contact with a hypochlorite solution.

The compounds/compositions can be dispensed by immersing either intermittently or continuously in water. The composition can then dissolve, for example, at a controlled or predetermined rate. The rate can be effective to maintain a concentration of dissolved agent that is effective for use according to the methods disclosed herein.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, n-propyl, isopropyl, n-butyl, iso-butyl, secondary-butyl, and tertiary-butyl. Alkyl groups may be unsubstituted or substituted by one or more suitable substituents, as defined above.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above.

The term "alkoxy," as used herein, refers to an alkyl group, as defined herein, appended to the parent molecular moiety through an oxygen atom.

The term "aryl," as used herein, means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined above.

The term "halo" or "halogen," as used herein, refers to a fluoro, chloro, bromo or iodo radical.

The term "heteroaryl," as used herein, refers to a monocyclic, bicyclic, or tricyclic aromatic heterocyclic group containing one or more heteroatoms (e.g., 1 to 3 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by one or more suitable substituents, preferably 1 to 5 suitable substituents, as defined above.

The term "heterocycle" or "heterocyclyl," as used herein, refers to a monocyclic, bicyclic, or tricyclic group containing 1 to 4 heteroatoms selected from N, O, $S(O)_n$, $P(O)_n$, $PR_z$, NH or $NR_z$, wherein $R_z$ is a suitable substituent. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, preferably 1 to 3 suitable substituents, as defined above.

The term "hydroxy," as used herein, refers to an —OH group.

The term "suitable substituent," as used herein, is intended to mean a chemically acceptable functional group, preferably a moiety that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, and arylsulfonyl groups. Those skilled in the art will appreciate that many substituents can be substituted by additional substituents.

The term "water cut," as used herein, means the percentage of water in a composition containing an oil and water mixture.

Having described the invention in detail, it will be apparent that modifications and variations are possible without departing from the scope of the invention defined in the appended claims.

EXAMPLES

The following non-limiting examples are provided to further illustrate the invention.

Example 1: Synthesis of Amine Epoxide Adducts

The synthesis of the amine epoxide adducts was achieved through a one-step ring opening reaction of an aromatic amine compound with an alkyl epoxide. Identities and mole ratios of the reagents are shown in Table 1.

TABLE 1

Reagents for synthesis of amine epoxide adducts

| Amine epoxide adduct identifier | Aromatic amine | Alkyl epoxide | Amine:Epoxide mole ratio |
|---|---|---|---|
| AEA1 | 4-aminophenol | Butylglycidyl ether | 1:2 |
| AEA2 | 4-aminophenol | 2-Ethylhexylglycidyl ether | 1:2 |
| AEA3 | 4-phenylenediamine | Butylglycidyl ether | 1:3 |
| AEA4 | N-phenyl-phenylenediamine | Butylglycidyl ether | 1:2 |

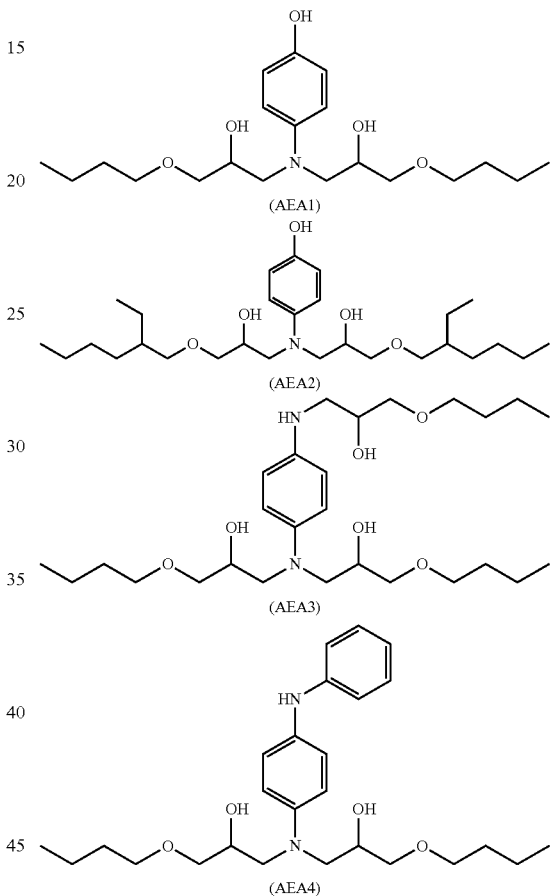

Example 2: Synthesis of 4-aminophenol-butylglycidyl ether (AEA1)

To a 250 mL three necked round-bottom flask equipped with a temperature probe, nitrogen inlet, condenser and magnetic stir bar was added butylglycidyl ether (95% purity, 49.2 g, 0.359 mol). 4-Aminophenol (98% purity, 20 g, 0.180 mol) was then added to the well-stirred reaction mixture. The resulting suspension was heated to 120° C. under nitrogen blanket and stirred for 2 hours or until completion of the reaction. As the reaction proceeded to completion, the suspension converted to a homogenous dark-amber product. The product was characterized for purity and the confirmation of the structure.

Example 3: Synthesis of AEA2

To a 1 L three necked round-bottom flask equipped with a temperature probe, nitrogen inlet, condenser and magnetic stir bar was added 2-ethylhexylglycidyl ether (98% purity, 160 g, 1.43 mol). 4-Aminophenol (98% purity, 546.3 g, 2.87 mol) was then added to the well-stirred reaction mixture. The resulting suspension was heated to 120° C. under nitrogen blanket and stirred for 2 hours or until completion of the reaction. As the reaction proceeded to completion, the suspension converted to a homogenous dark-amber product. The product was characterized for purity and the confirmation of the structure.

Example 4: Synthesis of AEA3

To a 250 mL three necked round-bottom flask equipped with a temperature probe, nitrogen inlet, condenser and magnetic stir bar was added butylglycidyl ether (98% purity, 38.1 g, 0.34 mol). p-phenylenediamine (98% purity, 141.4 g, 1.03 mol) was then added to the well-stirred reaction mixture. The resulting suspension was heated to 120° C. under nitrogen blanket and stirred for 2 hours or until completion of the reaction. As the reaction proceeded to completion, the suspension converted to a homogenous dark-amber product. The product was characterized for purity and the confirmation of the structure.

Example 5: Synthesis of AEA

To a 250 mL three necked round-bottom flask equipped with a temperature probe, nitrogen inlet, condenser and magnetic stir bar was added butylglycidyl ether (95% purity, 52.4 g, 0.38 mol). N-Phenyl-phenylenediamine (98% purity, 36 g, 0.19 mol) was then added to the well-stirred reaction mixture. The resulting suspension was heated to 120° C. under nitrogen blanket and stirred for 2 hours or until completion of the reaction. As the reaction proceeded to completion, the suspension converted to a homogenous dark-amber product. The product was characterized for purity and the confirmation of the structure.

Example 6: Corrosion Bubble Cell Tests

The corrosion inhibition performance in a series of test solutions was measured by separate corrosion bubble cell tests. A $CO_2$ saturated solvent blend was prepared that contained 80% of a 3% NaCl brine and 20% of LVT-200 hydrocarbon. The series of test solutions was made where each test solution included 10% of a test chemistry and 1 wt % 2-mercaptoethanol in the solvent blend. The anticorrosion compounds listed in Table 1 were tested. Quaternary ammonium chloride and imidazoline that are commonly used corrosion inhibitors were used as controls.

The effect of the anticorrosion compounds was tested using standard bubble cell test procedures. The bubble test simulates low flow areas where little or no mixing of water and oil occurs. The test was conducted using the brine disclosed above. The brine was placed into kettles and purged with carbon dioxide. The brine was continually purged with carbon dioxide to saturate the brine prior to starting the test. After the test began, the test cell was blanketed with carbon dioxide one hour prior to electrode insertion and through the duration of the test to maintain saturation. The kettles were stirred at 100 revolutions per minute (rpm) for the duration of the test to maintain thermal equilibrium at 50° C. The corrosion rate was measured by Linear Polarization Resistance (LPR) techniques. The working electrode used was 1018 carbon steel. The counter and reference electrodes were both Hastelloy. The electrodes were all cleaned with solvent prior to testing. Data were collected for four hours before each of the compositions was dosed into its respective cell. Data were collected overnight.

After collecting baseline corrosion rates in the brine for 3 hours, the anticorrosion compounds were dosed into bubble cells. Four different anticorrosion compounds were tested. FIG. 1 depicts the corrosion rates (mpy) measured for anticorrosion compounds dosed at 20 ppm of the 10 wt. % composition prepared above. The final concentrations in the test cell were 2 ppm of the test chemistry and 0.2 ppm of 2-mercaptoethanol. Over time, the anticorrosion compounds disclosed herein show a decreased corrosion rate as compared to the blank and the incumbent corrosion inhibitors.

Results are shown in FIG. 1 and Table 2. The corrosion rates in bubble cell tests employing quaternary ammonium chloride or imidazoline (commonly used corrosion inhibitors) were reduced compared to the bubble cell test with no corrosion inhibitor (i.e. blank). However, the corrosion rates for bubble cell tests employing the anticorrosion compounds described herein were reduced significantly more than corrosion rates in the tests employing the quaternary ammonium chloride (e.g., dimethyl benzyl ammonium chloride (DMBA Cl)) or imidazoline (e.g., tall oil fatty acid (TOFA): diethylene triamine (DETA) imidazoline salted with acetic acid (TOFA:DETA)). Bubble cell tests using AEA1, AEA2, and AEA4 demonstrated about half the corrosion rate (e.g. about 2 fold increase in % protection) at 15 hours after addition of the anticorrosion compound compared to tests using a quaternary ammonium chloride. AEA3 demonstrated an about 5.5 fold decrease in corrosion rate (e.g. about 2.75 fold increase in % protection) at 15 hours after addition of the anticorrosion compound as compared to tests using quaternary ammonium chloride. AEA3 also demonstrated corrosion rates that mostly did not increase over time compared to other tests, indicating longer duration of corrosion protection.

TABLE 2

| Identifier | Test Chemistry | Amine: Epoxide mole ratio in test chemistry | 2-Mercaptoethanol in test cell (ppm) | Chemistry in test cell (ppm) | Corrosion rate 15 h after Cl injection (mpy) | % Protection |
|---|---|---|---|---|---|---|
| Blank | — | — | — | — | 500 | — |
| Quaternary ammonium chloride | Dimethyl benzyl ammonium chloride | — | 0.2 | 2 | 339 | 32 |
| Imidazoline | Imidazoline with acetic acid | — | 0.2 | 2 | 432 | 14 |
| AEA1 | 4-aminophenol + butylglycidyl ether | 1:2 | 0.2 | 2 | 178 | 64 |

TABLE 2-continued

| Identifier | Test Chemistry | Amine: Epoxide mole ratio in test chemistry | 2-Mercaptoethanol in test cell (ppm) | Chemistry in test cell (ppm) | Corrosion rate 15 h after Cl injection (mpy) | % Protection |
|---|---|---|---|---|---|---|
| AEA2 | 4-aminophenol + 2-ethylhexylglycidyl ether | | 1:2 | 0.2 | 2 | 181 |
| AEA3 | 4-phenylenediamine + butyldiglycidyl ether | 1:3 | 0.2 | 2 | 62 | 88 |
| AEA4 | N-phenyl-phenylenediamine + butyldiglycidyl ether | 1:2 | 0.2 | 2 | 186 | 63 |

The terms "comprise(s)," "include(s)," "having," "has," "can," "contain(s)," and variants thereof, as used herein, are intended to be open-ended transitional phrases, terms, or words that do not preclude the possibility of additional steps or components. The singular forms "a," "and," "the" and "said" include plural references unless the context clearly dictates otherwise. The present disclosure also contemplates other embodiments "comprising," "consisting of" and "consisting essentially of," the embodiments or elements presented herein, whether explicitly set forth or not.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A method for reducing, inhibiting, or preventing corrosion of a surface, the method comprising:

adding an anticorrosion compound of Formula 2 to a fluid in contact with the surface, wherein the surface comprises a metal, the anticorrosion compound of Formula 2 having a structure corresponding to:

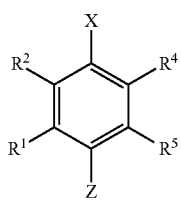

(2)

wherein Z has the structure corresponding to Z1 or Z2:

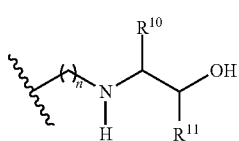

(Z1)

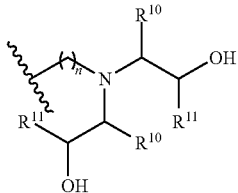

(Z2)

wherein
X is hydroxyl or —NHR$^9$;
n is 0;
R$^1$, R$^2$, R$^4$, and R$^5$ are independently hydrogen, hydroxyl, alkyl, alkoxyl, aryl, alkaryl, aralkyl, or —NR$^8$R$^9$ or any two adjacent groups of R$^1$, R$^2$, R$^4$, and R$^5$ form one or more ring structures;
R$^8$ and R$^9$ are independently hydrogen, unsubstituted alkyl, unsubstituted alkenyl, unsubstituted aryl, unsubstituted alkaryl, unsubstituted aralkyl, substituted alkyl, substituted alkenyl, or substituted alkaryl, wherein the substituted alkyl, substituted alkenyl, or substituted alkaryl are substituted with at least one hydroxyl or ether;
R$^{10}$ is independently hydrogen, alkyl, or aryl;
R$^{11}$ is alkyl, aryl, or —(CH$_2$)z-O—R$^{12}$;
R$^{12}$ is hydrogen or alkyl; and
z is an integer from 1 to 10.

2. The method of claim 1, wherein X is hydroxyl.

3. The method of claim 2, wherein Z corresponds to Z2, R$^{10}$ is hydrogen, and R$^{11}$ is —(CH$_2$)z-O—R$^{12}$, wherein z is 1 and R$^{12}$ is C$_4$ to C$_{10}$ alkyl.

4. The method of claim 1, wherein X is —NHR$^9$, wherein R$^9$ is phenyl.

5. The method of claim 4, wherein Z corresponds to Z2, R$^{10}$ is hydrogen, and R$^{11}$ is —(CH$_2$)z-O—R$^{12}$, wherein z is 1 and R$^{12}$ is C$_4$ to C$_{10}$ alkyl.

6. The method of claim 1, wherein Z corresponds to Z1 and R$^{10}$ is hydrogen; and R$^{11}$ is —(CH$_2$)z-O—R$^{12}$.

7. The method of claim 6, wherein z is 1 and R$^{12}$ is C$_4$ to C$_{10}$ alkyl.

8. The method of claim 7, wherein R$^{12}$ is butyl, pentyl, hexyl, heptyl, or octyl.

9. The method of claim 1, wherein Z is Z2.

10. The method of claim 9, wherein R$^{10}$ is hydrogen; and R$^{11}$ is —(CH$_2$)z-O—R$^{12}$.

11. The method of claim 10, wherein z is 1 and R$^{12}$ is alkyl.

12. The method of claim 11, wherein R$^{12}$ is C$_4$ to C$_{10}$ alkyl.

13. The method of claim 11, wherein $R^{12}$ is butyl, pentyl, hexyl, heptyl, or octyl.

14. The method of claim 1, wherein X is —$NHR^9$ and $R^9$ is substituted alkyl.

15. The method of claim 14, wherein Z corresponds to Z2, $R^{10}$ is hydrogen, and $R^{11}$ is —$(CH_2)z$-O—$R^{12}$, wherein z is 1 and $R^{12}$ is $C_4$ to $C_{10}$ alkyl.

16. The method of claim 1, wherein $R^1$, $R^2$, $R^4$, and $R^5$ are hydrogen.

17. The method of claim 1, wherein the anticorrosion compound of Formula 2 corresponds to:

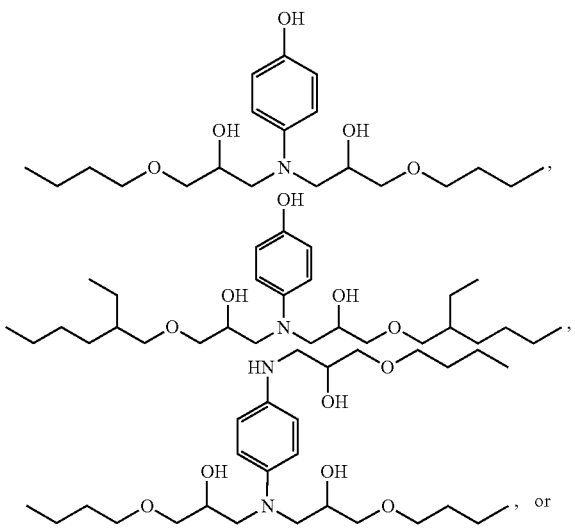

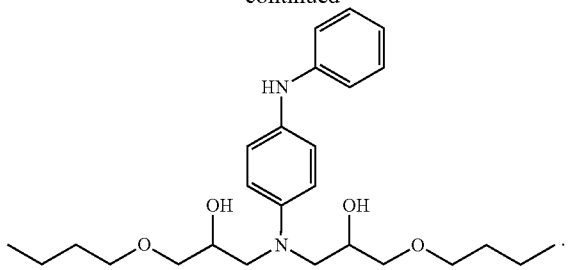

18. The method of claim 1, wherein the anticorrosion compound of Formula 2 is present in an amount from about 0.5 ppm to about 2500 ppm.

19. The method of claim 1, wherein the surface is part of equipment used in an industrial system and the industrial system is a water recirculating system, a cooling water system, a boiler water system, a petroleum well, a downhole formation, a geothermal well, a mineral washing system, a flotation and benefaction system, a papermaking system, a gas scrubber, an air washer, a continuous casting process in the metallurgical industry, an air conditioning and refrigeration system, a water reclamation system, a water purification system, a membrane filtration system, a food processing system, a clarifier system, a municipal sewage treatment system, a municipal water treatment system, or a potable water system.

* * * * *